United States Patent [19]

Albertson

[11] 3,936,462

[45] Feb. 3, 1976

[54] 1,2,3,4,5,6-HEXAHYDRO-1-OXO OR HYDROXY-3-ACYL-2,6-METHANO-3-BENZAZOCINES AND CORRESPONDING 1-ESTERS THEREOF

[75] Inventor: Noel F. Albertson, Schodack, N.Y.

[73] Assignee: Sterling Drug Inc., New York, N.Y.

[22] Filed: June 14, 1973

[21] Appl. No.: 369,870

Related U.S. Application Data

[63] Continuation-in-part of Ser. No. 257,343, May 26, 1972, Pat. No. 3,823,149, which is a continuation-in-part of Ser. No. 43,556, June 4, 1970, abandoned.

[52] U.S. Cl. .......................................... 260/293.54
[51] Int. Cl.² ...................................... C07D 221/26
[58] Field of Search ................ 260/293.54, DIG. 13

[56] References Cited
UNITED STATES PATENTS

| 3,634,433 | 1/1972 | Moriyama et al. | 260/DIG. 13 |
| 3,639,407 | 2/1972 | Clarke et al. | 260/DIG. 13 |

Primary Examiner—Sherman D. Winters
Attorney, Agent, or Firm—B. Woodrow Wyatt; Theodore C. Miller

[57] ABSTRACT 1,2,3,4,5,6-Hexahydro-1-oxo-3-(hydrocarbon or substituted hydrocarbon)-8-(H or OH)-6-(H or alkyl)-11-(H or alkyl)-2,6-methano-3-benzazocines and 1-hydroxy secondary and tertiary alcohols obtainable therefrom by reduction and by Grignard reactions, and esters of the same, are useful as central nervous system depressants, particularly as analgesics and as analgesic antagonists. The 3-substituent is introduced by alkylation, directly or by N-acylation followed by reduction of the resulting amides, of the corresponding >NH compounds either before or after introduction of the 1-oxo group into the compounds having two hydrogens at the 1-position by chromium (VI) oxidation. Various intermediates and derivatives are also descibed, including 3a,4,5,9b-tetrahydro-3,5-ethanonaphth[2,1-d]oxazol-2(3H)-ones obtained by interacting 1,2,3,4,5,6-hexahydro-1-hydroxy-2,6-methano-3-benzazocines with phosgene or by heating 1,2,3,4,5,6-hexahydro-1-hydroxy-3-carbalkoxy-2,6-methano-3-benzazocines with alkoxide ion.

11 Claims, No Drawings

1,2,3,4,5,6-HEXAHYDRO-1-OXO OR HYDROXY-3-ACYL-2,6-METHANO-3-BENZAZOCINES AND CORRESPONDING 1-ESTERS THEREOF

This application is a continuation-in-part of my prior co-pending application Ser. No. 257,343, filed May 26, 1972, issued July 9, 1974 as U.S. Patent 3,823,149, which in turn is a continuation-in-part of my prior co-pending application Ser. No. 43,556, filed June 4, 1970, now abandoned.

COMPOUNDS AND PREPARATION THEREOF

This invention relates to compositions of matter classified in the art of chemistry as 1,2,3,4,5,6-hexahydro-2,6-methano-3-benzazocines and 3a,4,5,9b-tetrahydro-3,5-ethanonaphth[2,1-d]-oxazol-2(3H)-ones, to processes for their preparation, and to intermediates for the same.

The compounds of this invention are useful as central nervous system depressants, more particularly being useful as analgesics and as antagonists of strong analgesics, such as meperidine, phenazocine, and morphine.

In the first of its composition of matter aspects, the invention sought to be patented resides in the novel chemical compounds designated as 1,2,3,4,5,6-hexahydro-1-($Y^1$)-1-($Y^2$)-3-(Q)-8-(Z)-6-($R^1$)-11-($R^2$)-2,6-methano-3-benzazocines having in the free base form the formula

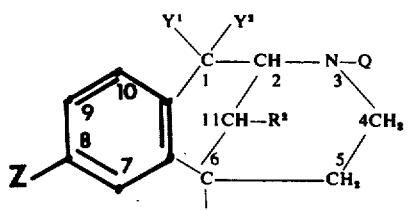

Formula I wherein:

$Y^1$ is hydroxy or acyloxy of the group consisting of: alkanoyloxy having 1–22 carbon atoms; alkenoyloxy having one or two double bonds and having 4–22 carbon atoms; Ar—$C_mH_{2m}$—CO—O— wherein m is an integer from zero to two and Ar is phenyl or is phenyl substituted by 1–3 members of the group consisting of alkyl having 1–4 carbon atoms, alkoxy having 1–4 carbon atoms, halo, trifluoromethyl, dialkylamino having 2–8 carbon atoms, and alkanoylamino having 1–6 carbon atoms; phenoxyacetoxy; naphthalenecarbonyloxy; pyridinecarbonyloxy; (cycloalkyl or fluorocycloalkyl)—$C_mH_{2m}$—CO—O— having a total of 4–10 carbon atoms of which 3–7 are ring carbon atoms in cycloalkyl and wherein m is an integer from zero to two, alkylcarbonate having 2–7 carbon atoms, carbamyloxy, or (mono- or di-alkyl)carbamyloxy having 2–9 carbon atoms;

$Y^2$ is hydrogen, alkyl having 1–6 carbon atoms, or $Ar^1$—$C_nH_{2n}$— wherein n is an integer from zero to four and $Ar^1$ is unsubstituted phenyl or phenyl substituted by 1–3 members of the group consisting of alkyl having 1–4 carbon atoms, alkoxy, having 1–4 carbon atoms, and dialkylamino having 2–8 carbon atoms; or $Y^1$ and $Y^2$ taken together represent oxo;

Q is a member of the group consisting of alkyl having 3–8 carbon atoms, alkenyl having 3–6 carbon atoms, haloalkenyl having 3–6 carbon atoms and having 1—3 members of the group consisting of chlorine, fluorine, and bromine attached to ethylenic carbon, cyanoalkyl having 2–6 carbon atoms, (mono- or di-cyano)alkenyl having 4–8 carbon atoms, 2,2-dialkoxyethyl having 4–8 carbon atoms, alkynyl having 3–6 carbon atoms, (cycloalkyl or fluorocycloalkyl)—$C_nH_{2n}$— wherein n is an integer from zero to four and wherein cycloalkyl has 3–7 ring carbon atoms and has a total of 3–10 carbon atoms, 2- or 3-cycloalkenyl wherein cycloalkenyl has 5–6 ring carbon atoms and has a total of 5–8 carbon atoms, cycloalkenyl—$C_pH_{2p}$— wherein p is an integer from one to four and wherein cycloalkenyl has 5–6 ring carbon atoms and has a total of 5–8 carbon atoms, and $Ar^2$—$C_pH_{2p}$— wherein p is an integer from one to four and $Ar^2$ is phenyl or is phenyl substituted by amino, nitro, alkanoylamino, having 1–6 carbon atoms, alkoxy having 1–4 carbon atoms, alkyl having 1–4 carbon atoms, halo, or trifluoromethyl, the member Q in each instance having no tertiary alpha-carbon atom;

Z is hydrogen, hydroxy, or one of the acyloxy groups defined by $Y^1$; and $R^1$ and $R^2$ are members of the group consisting of hydrogen and alkyl having 1–4 carbon atoms; and the acid-addition salts thereof.

In a second composition of matter aspect, the invention sought to be patented resides in certain novel chemical compounds designated as 1,2,3,4,5,6-hexahydro-1-oxo-3-(Q)-8-($Z^1$)-6-($R^1$)-11-($R^2$)-2,6-methano-3-benzazocines having in the free base form the formula

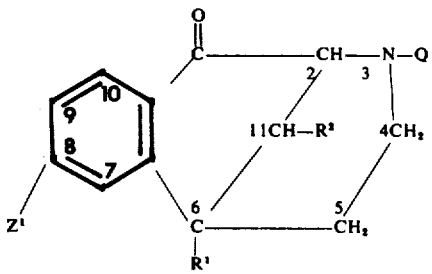

Formula II wherein:

Q, $R^1$, and $R^2$ have the same significance as in Formula I; and $Z^1$ is alkoxy having 1–6 carbon atoms, difluoromethoxy, trifluoromethoxy, benzyloxy, or alkenyloxy having 3–6 carbon atoms;

and the acid-addition salts thereof.

In a third composition of matter aspect, the invention sought to be patented resides in certain novel chemical compounds designated as 1,2,3,4,5,6-hexahydro-1-($Y^1$)-($Y^2$)-3-methyl-($Z^2$)-6-($R^1$)-11-($R^2$)-2,6-methano-3-benzazocines having in the free base form the formula

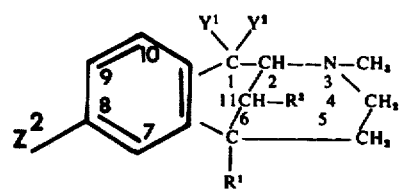

Formula III wherein $Y^1$ and $Y^2$ taken individually have the same significance as in Formula I; or $Y^1$ and $Y^2$ taken together represent oxo;

$R^1$ has the same significance as in Formula I;

$R^3$ is alkyl having 1–4 carbon atoms; and $Z^2$ is one of the members defined by Z in Formula I and by $Z^1$ in Formula II;

and the acid-addition salts thereof.

In a fourth composition of matter aspect, the invention sought to be patented resides in certain novel chemical compounds designated as 1,2,3,4,5,6-hexahydro-1-($Y^1$)-1-($Y^2$)-3-($Q^1$)-8-($Z^2$)-6-($R^1$)-11-($R^2$)-2,6-methano-3-benzazocines having in the free base form the formula

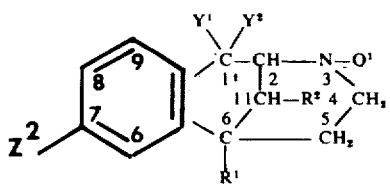

Formula IV wherein:

$Y^1$ and $Y^2$ taken individually have the same significance as in Formula I; or $Y^1$ and $Y^2$ taken together represent oxo;

$R^1$ and $R^2$ have the same significance as in Formula I;

$Z^2$ has the same significance as in Formula III; and $Q^1$ is a member of the group consisting of: carbalkoxy having 2–7 carbon atoms; carbobenzyloxy; and, when $Y^1$ and $Y^2$ taken together are oxo, N-(carbalkoxy)aminoacetyl having 4–9 carbon atoms and N-(carbobenzyloxy)aminoacetyl; and the acid-addition salts thereof.

In a fifth composition of matter aspect, the invention sought to be patented resides in the novel chemical compounds designated as 3a,4,5,9b-tetrahydro-7-($Z^2$)-9b-($Y^2$)-4-($R^2$)-5-($R^1$)-3,5-ethanonaphth[2,1-d]oxazol-2-(3H)-ones having the formula

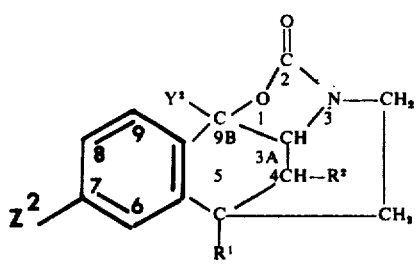

Formula V wherein:

$Y^2$, $R^1$, and $R^2$ have the same significance as in Formula I; and $Z^2$ has the same significance as in Formula III; and the acid-addition salts thereof.

In a sixth composition of matter aspect, the invention sought to be patented resides in the novel chemical compounds designated as 1,2,3,4,5,6-hexahydro-1-($Y^1$)-1-($Y^2$)-8-($Z^2$)-6-($R^1$)-11-($R^2$)-2,6-methano-3-benzazocines having in the free base form the formula

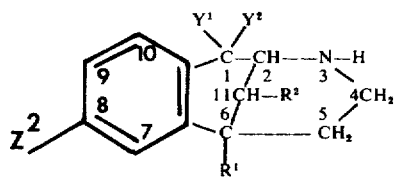

Formula VI wherein:

$Y^1$ and $Y^2$ taken individually have the same significance as in Formula I; or $Y^1$ and $Y^2$ taken together represent oxo;

$R^1$ and $R^2$ have the same significance as in Formula I; and $Z^2$ has the same significance as in Formula III; and the acid-addition salts thereof.

In a seventh composition of matter aspect, the invention sought to be patented resides in certain novel chemical compounds designated as 1,2,3,4,5,6-hexahydro-1-($Y^1$)-1-($Y^2$)-3-($Q^2$-CO-)-8-($Z^2$)-6-($R^1$)-11-($R^2$)-2,6-methano-3-benzazocines having the formula

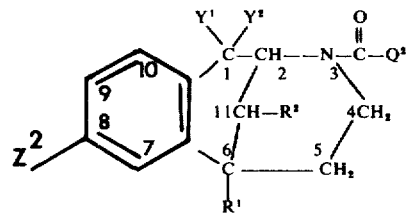

Formula VII wherein:

$R^1$, and $R^2$ have the same significance as in Formula I;

$Y^1$ and $Y^2$ have the same significance as in Formula I; or $Y^1$ and $Y^2$ taken together represent oxo or a ketal thereof;

$Z^2$ has the same significance as in Formula III; and $Q^2$ is alkyl having 1–7 carbon atoms, alkenyl having 2–5 carbon atoms, haloalkenyl having 2–5 carbon atoms and having 1–3 members of the group consisting of chlorine, fluorine, and bromine attached to ethylenic carbon, alkynyl having 2–5 carbon atoms, cycloalkyl—$C_qH_{2q}$— wherein q is an integer from zero to three and wherein cycloalkyl has 3–7 ring carbon atoms and has a total of 3–10 carbon atoms, and $Ar^2$—$C_qH_{2q}$— wherein q is an integer from zero to three and $Ar^2$ is phenyl or is phenyl substituted by amino, nitro, alkanoylamino having 1–6 carbon atoms, alkoxy having 1–4 carbon atoms, alkyl having 1–4 carbon atoms, halo, or trifluoromethyl.

In the first of its process aspects, the invention sought to be patented resides in the process which comprises reacting 1,2,3,4,5,6-hexahydro-1-($Y^1$)-1-($Y^2$)-8-($Z^2$)-6-($R^1$)-11-($R^2$)-2,6-methano-3-benzazocine with an alkylating agent having the formula $Q^3$—An in the presence of an acid-absorbing medium, to yield 1,2,3,4,5,6-hexahydro-1-($Y^1$)-1-($Y^2$)-3-($Q^3$)-8-($Z^2$)-6-($R^1$)-11-($R^2$)-2,6-methano-3-benzazocine, wherein:

$Y^1$ and $Y^2$ taken individually have the same significance as in Formula I; or $Y^1$ and $Y^2$ taken together represent oxo;

$R^1$ and $R^2$ have the same significance as in Formula I;

$Z^2$ has the same significance as in Formula III;

An is the anion of a strong organic or inorganic acid; and $Q^3$ is methyl, ethyl, or one of the members defined by Q in Formula I except those members wherein $Ar^2$ is aminophenyl.

In a second process aspect, the invention sought to be patented resides in the process which comprises oxidizing 1,2,3,4,5,6-hexahydro-3-($Q^4$)-8-($Z^3$)-6-($R^1$)-11-($R^2$)-2,6-methano-3-benzazocine, having the formula

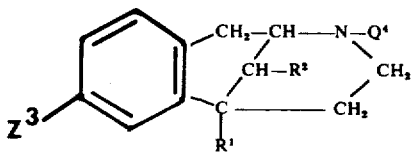

Formula VIII with chromium(VI) in acid medium to yield 1,2,3,4,5,6-hexahydro-1-oxo-3-($Q^4$)-8-($Z^3$)-6-($R^1$)-11-($R^2$)-2,6-methano-3-benzazocine having the formula

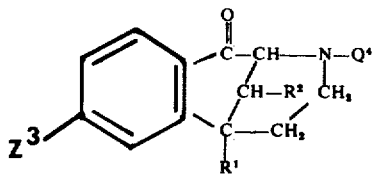

Formula IX wherein in each of Formulas VIII and IX:

$R^1$ and $R^2$ have the same significance as in Formula I;

$Q^4$ is hydrogen, methyl, ethyl, alkyl having 3–8 carbon atoms, 2,2-dialkoxyethyl having 4–8 carbon atoms, (cycloalkyl or fluorocycloalkyl)—$C_nH_{2n}$— wherein n is an integer from zero to four and wherein cycloalkyl has 3–7 carbon atoms and has a total of 3–10 carbon atoms, and $Ar^3$—$C_rH_{2r}$— wherein r is an integer from two to four and $Ar^3$ is phenyl or is phenyl substituted by nitro, alkanoyl-amino having 1–6 carbon atoms, alkoxy having 1–4 carbon atoms, alkyl having 1–4 carbon atoms, halo, or trifluoromethyl; and $Z^3$ is hydrogen, alkoxy having 1–6 carbon atoms, or alkenyloxy having 3–6 carbon atoms.

In a third process aspect, the invention sought to be patented resides in the process which comprises reducing 1,2,3,4,5,6-hexahydro-1-oxo-3-($Q^5$)-8-($Z^2$)-6-($R^1$)-11-($R^2$)-2,6-methano-3-benzazocine with reducing means effective to convert the 1—oxo group to a 1—hydroxyl group without affecting any cyano groups or ethylenic linkages which are present, wherein:

$R^1$ and $R^2$ each have the same significance as in Formula I;

$Z^2$ has the same significance as in Formula III; and $Q^5$ is hydrogen, methyl, ethyl, or one of the members defined by Q in Formula I.

In a fourth process aspect, the invention sought to be patented resides in the process which comprises reacting in a Grignard reaction 1,2,3,4,5,6-hexahydro-1-oxo-3-($Q^6$)-8-($Z^3$)-6-($R^1$)-11-($R^2$)-2,6-methano-3-benzazocine with a Grignard reagent having the formula $Y^3$—Mg—halogen to yield 1,2,3,4,5,6-hexahydro-1-hydroxy-1-($Y^3$)-3-($Q^6$)-8-($Z^3$)-6-($R^1$)-11-($R^2$)-2,6-methano-3-benzazocine, wherein:

$Y^3$ is one of the members of $Y^2$ in Formula I other than hydrogen;

$R^1$ and $R^2$ have the same significance as in Formula I;

$Z^3$ has the same significance as in Formula IX; and $Q^6$ is a member of the group consisting of hydrogen, alkyl having 1–8 carbon atoms, alkenyl having 3–6 carbon atoms, haloalkenyl having 3–6 carbon atoms and having 1–3 members of the group consisting of chlorine, fluorine, and bromine attached to ethylenic carbon, alkynyl having 3–6 carbon atoms, (cycloalkyl or fluorocycloalkyl)—$C_nH_{2n}$— wherein n is an integer from zero to four and wherein cycloalkyl has 3–7 ring carbon atoms and has a total of 3–10 carbon atoms, 2— or 3—cycloalkenyl wherein cycloalkenyl has 5–6 ring carbon atoms and has a total of 5–8 carbon atoms, cycloalkenyl—$C_pH_{2p}$— wherein p is an integer from one to four and wherein cycloalkenyl has 5–6 carbon atoms and has a total of 5–8 carbon atoms, and $Ar^4$—$C_pH_{2p}$— wherein p is an integer from one to four and $Ar^4$ is phenyl or phenyl substituted by alkyl having 1–4 carbon atoms or alkoxy having 1–4 carbon atoms, the member $Q^6$ in each instance having no tertiary alpha-carbon atom.

In a fifth process aspect, the invention sought to be patented resides in the process which comprises N-acylating 1,2,3,4,5,6-hexahydro-1-($Y^1$)-1-($Y^2$)-8-($Z^2$)-6-($R^1$)-11-($R^2$)-2,6-methano-3-benzazocine by treatment with an active acylating form, such as an acid halide, acid anhydride, or mixed anhydride, of an acid having the formula $Q^7$—COOH to yield 1,2,3,4,5,6-hexahydro-1-($Y^4$)-1-($Y^2$)-3-($Q^7$-CO-)-8-($Z^4$)-6-($R^1$)-11-($R^2$)-2,6-methano-3-benzazocine, wherein:

$Y^1$ and $Y^2$ taken individually have the same significance as in Formula I; or $Y^1$ and $Y^2$ taken together represent oxo;

$R^1$ and $R^2$ have the same significance as in Formula I;

$Z^2$ has the same significance as in Formula III;

$Y^4$ has the same significance as $Y^1$ in Formula I or is $Q^7$—CO—O—;

$Z^4$ has the same significance as $Z^2$ in Formula III or is $Q^7$—CO—O—; and $Q^7$ in each instance has the same significance as $Q^2$ in Formula VII except that $Ar^2$ does not include aminophenyl.

In a sixth process aspect, the invention sought to be patented resides in the process which comprises reducing 1,2,3,4,5,6-hexahydro-1-($Y^5$)-1-($Y^2$)-3-($Q^2$-CO-)-8-($Z^5$)-6-($R^1$)-11-($R^2$)-2,6-methano-3-benzazocine with a reducing agent effective to reduce the carbonyl of the N-acyl group to a methylene group (i.e. —$CH_2$—) without affecting any ethylenic linkages, thereby producing 1,2,3,4,5,6-hexahydro-1-hydroxy-1-($Y^2$)-3-($Q^8$-$CH_2$-)-8-($Z^5$)-6-($R^1$)-11-($R^2$)-2,6-methano-3-benzazocine, wherein:

$Y^2$, $R^1$, and $R^2$ have the same significance as in Formula I;

$Y^5$ has the same significance as in Formula I or is $Q^2$—CO—O—;

$Q^2$ in each instance has the same significance as in Formula VII; and $Q^6$ is the same as $Q^2$ except that $Ar^2$ does not include nitrophenyl; and $Z^5$ has the same significance as $Z^2$ in Formula III or is $Q^2$—CO—O—.

In a seventh process aspect, the invention sought to be patented resides in the process which comprises reacting 1,2,3,4,5,6-hexahydro-1(eq)-hydroxy-1-($Y^2$)-8-($Z^2$)-6-($R^1$)-11-($R^2$)-2,6-methano-3-benzazocine with phosgene to yield 3a,4,5,9b-tetrahydro-7-($Z^2$)-9b-($Y^2$)-4-($R^2$)-5-($R^1$)-3,5-ethanonaphth[2,1-d]oxazol-2(3H)-one wherein:

$Y^2$, $R^1$, $R^2$ have the same significance as in Formula I; and $Z^2$ has the same significance as in Formula III.

In an eighth process aspect, the invention sought to be patented resides in the process which comprises heating 1,2,3,4,5,6-hexahydro-1(eq)-hydroxy-1-($Y^2$)-3-(carbalkoxy)-8-($Z^2$)-6-($R^1$)-11-($R^2$)-2,6-methano-3-benzazocine in the presence of a catalytic amount of alkoxide ion to yield 3a,4,5,9b-tetrahydro-7-($Z^2$)-9b-($Y^2$)-4-($R^2$)-5-($R^1$)-3,5-ethanonaphth[2,1-d]oxazol-2(3H)-one wherein:

$Y^2$, $R^1$, and $R^2$ have the same significance as in Formula I;

$Z^2$ has the same significance as in Formula III; and carbalkoxy has 2–7 carbon atoms.

When $Y^1$, $Y^4$, Z, $Z^2$, and $Z^4$ in the formulas herein are alkanoyloxy there are included, for example, formyloxy, acetoxy, propionyloxy, butyryloxy, isobutyryloxy, valeryloxy, isovaleryloxy, 2-methylbutanoyloxy, pivalyloxy, 3-methylpentanoyloxy, 3,3-dimethylbutanoyloxy, 2,2-dimethylpentanoyloxy, docosanoyloxy, 7,7-dimethyloctanoyloxy, and the like. When $Y^1$, $Y^4$, Z, $Z^2$, and $Z^4$ in the formulas herein are alkenoyloxy there are included, for example, crotonyloxy, 9-octadecenoyloxy, 2,5-hexadienoyloxy, 3,6-octadienoyloxy, 10,13-octadecadienoyloxy, 5,13-docosadienoyloxy, and the like.

When $Y^1$, $Y^4$, Z, $Z^2$, and $Z^4$ in the formulas herein are Ar—$C_mH_{2m}$CO—O— there are included, for example, benzoyloxy, p-toluyloxy, m-toluyloxy, o-toluyloxy, o-ethylbenzoyloxy, p-tert-butylbenzoyloxy, 3,4-dimethylbenzoyloxy, 2-methyl-4-ethylbenzoyloxy, 2,4,6-trimethylbenzoyloxy, p-anisoyloxy, m-anisoyloxy, o-anisoyloxy, m-isopropoxybenzoyloxy, p-n-butoxybenzoyloxy, 3-methoxy-4-ethoxybenzoyloxy, 3,4,5-trimethoxybenzoyloxy, 2,4,6-triethoxybenzoyloxy, o-iodobenzoyloxy, m-bromobenzoyloxy, p-chlorobenzoyloxy, p-fluorobenzoyloxy, 2-bromo-4-chlorobenzoyloxy, 2,4,6-trichlorobenzoyloxy, p-trifluoromethylbenzoyloxy, 2,4-di(trifluoromethyl)benzoyloxy, 2-methyl-4-methoxybenzoyloxy, 3-chloro-4-ethoxybenzoyloxy, p-dimethylaminobenzoyloxy, m-diethylaminobenzoyloxy, p-dibutylaminobenzoyloxy, p-(N-methyl-N-ethylamino)benzoyloxy, o-acetamidobenzoyloxy, m-propionamidobenzoyloxy, p-hexanoylaminobenzoyloxy, phenylacetoxy, alpha-phenylpropionyloxy, beta-phenylpropionyloxy, m-methylphenylacetoxy, p-isobutylphenylacetoxy, beta-(p-ethylphenyl)propionyloxy, p-methoxyphenylacetoxy, m-isobutoxyphenylacetoxy, 3,4-diethoxyphenylacetoxy, beta-(3,4,5-trimethoxyphenyl)-propionyloxy, p-chlorophenylacetoxy, alpha-(m-bromophenyl)propionyloxy, m-trifluoromethylphenylacetoxy, beta-(p-trifluoromethylphenyl)propionyloxy, beta-(3-methyl-4-chlorophenyl)propionyloxy, 3-chloro-4-acetamidophenylacetoxy, beta-(p-acetamidophenyl)propionyloxy, and the like.

When $Y^1$, $Y^4$, Z, $Z^2$, and $Z^4$ in the formulas herein are naphthalenecarbonyloxy there are included 1-naphthalenecarbonyloxy and 2-naphthalenecarbonyloxy.

When $Y^1$, $Y^4$, Z, $Z^2$, and $Z^4$ in the formulas herein are pyridinecarbonyloxy there are included picolinoyloxy (2-pyridinecarbonyloxy), nicotinoyloxy (3-pyridinecarbonyloxy), and isonicotinoyloxy (4-pyridinecarbonyloxy).

When $Y^1$, $Y^4$, Z, $Z^2$, and $Z^4$ in the formulas herein are (cycloalkyl or fluorocycloalkyl)—$C_mH_{2m}$—CO—O— there are included, for example, cyclopropanecarbonyloxy, 1-methylcyclopropanecarbonyloxy, 2-hexylcyclopropanecarbonyloxy, 2-methylcyclopropanecarbonyloxy, 1,3-dimethylcyclobutanecarbonyloxy, 3,3-dimethylcyclobutanecarbonyloxy, cyclopentanecarbonyloxy, 1-methyl-3-isopropylcyclopentanecarbonyloxy, cyclohexanecarbonyl, cycloheptanecarbonyloxy, alpha-methylcyclopropaneacetoxy, 1-methylcyclopropaneacetoxy, 2-amylcyclopropaneacetoxy, cyclopropanepropionyloxy, alpha-methylcyclopropanepropionyloxy, 2-isobutylcyclopropanepropionyloxy, cyclobutanepropionyloxy, cyclobutanepropionyloxy, cyclopentanepropionyloxy, cyclohexaneacetoxy, 4-methylcyclohexaneacetoxy, 4-methylcycloheptaneacetoxy, cycloheptanepropionyloxy, 1-fluorocyclopropanecarbonyloxy, 2-fluorocyclopropanecarbonyloxy, 1,2-difluorocyclopropanecarbonyloxy, 2,2-difluorocyclopropanecarbonyloxy, 3,3-difluorocyclohexanecarbonyloxy, 3-(1,3-difluorocyclohexanecarbonyloxy), and the like.

When $Y^1$, $Y^4$, Z, $Z^2$, and $Z^4$ in the formulas herein are alkylcarbonato there are included, for example, methylcarbonato, ethylcarbonato, isopropylcarbonato, amylcarbonato, 3,3-dimethylbutylcarbonato, and the like.

When $Y^1$, $Y^4$, Z, $Z^2$, and $Z^4$ in the formulas herein are (mono- or di-alkyl)carbamyloxy there are included, for example, methylcarbamyloxy, ethylcarbamyloxy, tert-butylcarbamyloxy, octylcarbamyloxy, dimethylcarbamyloxy, N-methyl-N-ethylcarbamyloxy, dibutylcarbamyloxy, and the like.

When $Y^2$ and $Y^3$ in the formulas herein are alkyl having 1–6 carbon atoms there are included, for example, methyl, ethyl, isopropyl, tert-butyl, amyl, hexyl, 2,3-dimethylbutyl, and the like.

When $Y^2$ and $Y^3$ in the formulas herein are Ar-$^1$—$C_nH_{2n}$— there are included, for example, phenyl, benzyl, p-tolyl, m-tolyl, o-tolyl, m-ethylbenzyl, m-tert-butylbenzyl, 3,5-dimethylbenzyl, 3-methyl-4-ethylbenzyl, 2,4,6-trimethylbenzyl, p-methoxybenzyl, m-methoxybenzyl, m-propoxybenzyl, p-tert-butoxybenzyl, 3-methoxy-4-ethoxybenzyl, p-methoxyphenyl, o-methoxyphenyl, 3,4,5-trimethoxyphenyl, 2,4,6-triethoxyphenyl, 2-methyl-4-methoxyphenyl, p-dimethylaminophenyl, m-diethylaminophenyl, p-dibutylaminophenyl, p-(N-methyl-N-ethylamino)phenyl, phenethyl, alpha-phenylpropyl, beta-phenylpropyl, m-methylphenethyl, p-isobutylphenethyl, beta-(p-ethylphenyl)propyl, p-methoxyphenethyl, m-isobutoxyphenethyl, 3,4-diethoxyphenethyl, beta-(3,4,5-trimethoxyphenyl)propyl, and the like.

The groups Q, $Q^3$, $Q^4$, $Q^5$, and $Q^6$ as used herein have no tertiary alpha-carbon atom, i.e. the carbon atom in these monovalent groups bearing the free valence bond (which is of course attached to the nitrogen atom in the respective compounds involved) has at least one hydrogen atom attached to it.

When Q, $Q^3$, $Q^4$, and $Q^5$ as used herein are alkyl having 3–8 carbon atoms there are included, for example, propyl, isopropyl, butyl, sec-butyl, amyl, hexyl, isohexyl, heptyl, 3-methylhexyl, octyl, 2,4-dimethylhexyl, isooctyl, and the like.

When Q, $Q^3$, $Q^5$, and $Q^6$ in the formulas herein are alkenyl there are included, for example, allyl; 2-methyl-2-propenyl, 2-butenyl, 4-pentenyl, 3-methyl-2-butenyl, 2-hexenyl, 3-hexenyl, 1-methyl-2-propenyl, 1,3-dimethyl-2-butenyl, and the like.

When Q, $Q^3$, $Q^5$, and $Q^6$ in the formulas herein are haloalkenyl there are included, for example, 3-chloro-2-butenyl, 2,3-dichloro-2-butenyl, 2-bromo-2-butenyl, 2,3-difluoro-3-chloro-2-propenyl, 2-chloro-2-propenyl, 2-bromo-2-propenyl, 2-fluoro-2-propenyl, 3-chloro-2-propenyl, 3-bromo-2-propenyl, 3,3-difluoro-2-propenyl, 2,3-difluoro-2-propenyl, 4-chloro-3-pentenyl, 2-chloro-3-methyl-2-butenyl, 5-bromo-5-hexenyl, and the like.

When Q, $Q^3$, and $Q^5$ in the formulas herein are cyanoalkyl there are included, for example, cyanomethyl, 2-cyanoethyl, 2-cyanopropyl, 4-cyanobutyl, and the like.

When Q, $Q^3$, and $Q^5$ in the formulas herein are (mono- or di-cyanoalkenyl) there are included, for example, 3-cyano-2-propenyl, 4-cyano-2-butenyl, 4-cyano-3-butenyl, 3-cyano-3-butenyl, 5-cyano-2-pentenyl, 3,3-dicyano-2-propenyl, 2,3-dicyano-2-butenyl, and the like.

When Q, $Q^3$, $Q^4$, and $Q^5$ as used herein are 2,2-dialkoxyethyl there are included, for example, 2,2-dimethoxyethyl, 2,2-diethoxyethyl, 2,2-diisopropoxyethyl, 2,2-dibutoxyethyl, and the like.

When Q, $Q^3$, $Q^5$, and $Q^6$ in the formulas herein are alkynyl there are included, for example, propargyl, 2-butynyl, 2-pentynyl, 3-pentynyl, 3-methyl-2-pentynyl, and the like.

When Q, $Q^3$, $Q^4$, $Q^5$, and $Q^6$ in the formulas herein are (cycloalkyl or fluorocycloalkyl)—$C_nH_{2n}$— there are included, for example, cyclopropyl, cyclobutyl, cyclopentyl, cyclohexyl, cycloheptyl, 1-methylcyclopropyl, 2-methylcyclobutyl, 2,2-dimethylcyclobutyl, 3,3-diethylcyclohexyl, cyclopropylmethyl, cyclobutylmethyl, cyclopentylmethyl, cyclohexylmethyl, cycloheptylmethyl, 2-cyclopentylethyl, 3-cyclohexylbutyl, (1-fluorocyclopropyl)methyl, 2-fluorocyclopropylmethyl, (1,2-difluorocyclopropyl)methyl, 2,2-difluorocyclopropylmethyl, 2,2,3-trifluorocyclopropylmethyl, 2,2,3,3-tetrafluorocyclopropylmethyl, 2-fluorocyclobutylmethyl, 3,3-difluorocyclohexylmethyl, 3-(1,3-difluorocyclohexyl)propyl, and the like.

When Q, $Q^3$, $Q^5$, and $Q^6$ in the formulas herein are 2- or 3-cycloalkenyl there are included, for example, 2-cyclopentenyl, 3-cyclopentenyl, 4-methyl-2-cyclopentenyl, 3-ethyl-3-cyclopentenyl, 2-cyclohexenyl, 3-cyclohexenyl, 3,4-dimethyl-2-cyclohexenyl, and the like.

When Q, $Q^3$, $Q^5$, and $Q^6$ in the formulas herein are cycloalkenyl—$C_pH_{2p}$— there are included, for example, 1-cyclopentenylmethyl, 2-cyclopentenylmethyl, 2-(3-cyclopentenyl)ethyl, 4-(2-cyclopentenyl)butyl, 3-(3-ethyl-2-cyclohexenyl)propyl, 1-cyclohexenylmethyl, 2-cyclohexenylmethyl, and the like.

When Q, $Q^3$, and $Q^5$ in the formulas herein are Ar$^2$—$C_pH_{2p}$— there are included, for example, benzyl, p-tolylmethyl, o-tolylmethyl, m-tolylmethyl, 2,4-dimethylbenzyl, phenethyl, p-methylphenethyl, 3-(m-ethylphenyl)butyl, p-aminobenzyl, p-aminophenethyl, 4-(o-aminophenyl)butyl, p-nitrobenzyl, m-nitrobenzyl, p-nitrophenethyl, 3-(m-nitrophenyl)butyl, p-acetamidobenzyl, m-acetamidobenzyl, p-acetamidophenethyl, 3-(m-hexanoylaminophenyl)propyl, p-methoxybenzyl, p-ethoxyphenethyl, 3-(m-isobutoxyphenyl)butyl, 3,4-dimethoxybenzyl, 2,4-dimethoxyphenethyl, p-chlorobenzyl, m-fluorophenethyl, 4-(o-bromophenyl)butyl, p-iodobenzyl, p-trifluoromethylphenethyl, and the like.

When $Q^1$ as used herein is carbalkoxy having 2–7 carbon atoms there are included, for example, carbomethoxy, carbethoxy, carbopropoxy, carbo-tert-butoxy, carboheptoxy, and the like.

When $Q^1$ as used herein is carbobenzyloxy, the phenyl group therein can if desired bear 1–3 substituents such as alkoxy having 1–4 carbon atoms, alkyl having 1–4 carbon atoms, and the like, p-methoxybenzyloxy being particularly preferred.

When $Q^1$ as used herein is N-(carbalkoxy)aminoacetyl there are included, for example, N-(carbomethoxy)aminoacetyl, N-(carbethoxy)aminoacetyl, N-(carbopropoxy)aminoacetyl, N-(carbo-tert-butoxy)aminoacetyl, N-(carboheptoxy)aminoacetyl, and the like.

When $Q^1$ as used herein is N-(carbobenzyloxy)aminoacetyl the phenyl group therein can if desired bear 1–3 substituents such as alkoxy having 1–4 carbon atoms, alkyl having 1–4 carbon atoms, and the like, N-(p-methoxybenzyloxy)aminoacetyl being particularly preferred.

When $Q^2$ as used herein is alkyl there are included, for example, methyl, ethyl, propyl, isopropyl, tert-butyl, isoamyl, hexyl, heptyl, 2-ethylpentyl, and the like.

When $Q^2$ as used herein is alkenyl there are included, for example, vinyl, allyl, 1-methylvinyl, 1-propenyl, 3-butenyl, 1-methyl-1-propenyl, 1-pentenyl, 2-pentenyl, 1-methyl-2-propenyl, 1,2-dimethyl-1-propenyl, and the like.

When $Q^2$ as used herein is haloalkenyl there are included, for example, 2-chloro-1-propenyl, 3-chloro-2-propenyl, 1,2-dichloro-1-propenyl, 1-bromo-1-propenyl, 1-chlorovinyl, 1-fluorovinyl, 2,2-difluorovinyl, 1,2-difluorovinyl, 1,2-difluoro-2-chlorovinyl, 3-chloro-2-butenyl, 1-chloro-2-methyl-1-propenyl, 4-bromo-4-pentenyl, and the like.

When $Q^2$ as used herein is alkynyl there are included, for example, ethynyl, 1-propynyl, 1-butynyl, 2-butynyl, 2-methyl-1-butynyl, and the like.

When $Q^2$ as used herein is cycloalkyl—$C_qH_{2q}$— there are included, for example, cyclopropyl, cyclobutyl, cyclopentyl, cyclohexyl, cycloheptyl, 1-methylcyclopropyl, 2-methylcyclobutyl, 2,2-dimethylcyclobutyl, 3,3-diethylcyclohexyl, cyclopropylmethyl, cyclobutylmethyl, cyclopentylmethyl, cyclohexylmethyl, cycloheptylmethyl, 2-cyclopentylethyl, 3-cyclohexylpropyl, and the like.

When $Q^2$ as used herein is Ar$^2$—$C_qH_{2q}$— there are included, for example, phenyl, p-tolyl, o-tolyl, m-tolyl, 2,4-dimethylphenyl, benzyl, p-methylbenzyl, 3-(m-ethylphenyl)propyl, p-aminophenyl, m-aminophenethyl, p-amino-benzyl, 3-(o-aminophenyl)propyl, p-nitrophenyl, m-nitrophenyl, p-nitrobenzyl, 2-(m-nitrophenyl)propyl, p-methoxyphenyl, p-ethoxybenzyl, 3-(m-isobutoxyphenyl)propyl, 3,4-dimethoxyphenyl, 2,4-dimethoxybenzyl, 3,4,5-trimethoxyphenyl, p-chlorophenyl, m-fluorophenyl, p-trifluoromethylphenyl, m-chlorobenzyl, p-bromobenzyl, 3-(o-bromophenyl)propyl, p-iodophenyl, m-trifluoromethylbenzyl, and the like. When $Q^7$ is one of the members defined by $Q^2$ there are included, for example, all of the above except those members wherein $Ar^2$ is aminophenyl.

When $Q^4$ as herein is $Ar^3$—$C_rH_{2r}$— there are included, for example, phenethyl, p-methylphenethyl, 3-(m-ethylphenyl)butyl, p-nitrophenethyl, 3-(m-nitrophenyl)butyl, p-acetamidophenethyl, 3-(m-hexanoylaminophenyl)propyl, p-ethoxyphenethyl, 3-(m-isobutoxyphenyl)butyl, 2,4-dimethoxyphenethyl, p-chlorophenethyl, m-fluorophenethyl, 4-(o-bromophenyl)butyl, p-trifluoromethylphenethyl, and the like.

When $Q^6$ as used herein is alkyl there are included, for example, methyl, ethyl, propyl, isopropyl, butyl, sec-butyl, amyl, hexyl, isohexyl, heptyl, 3-methylhexyl, octyl, 2,4-dimethylhexyl, isooctyl, and the like.

When $Q^6$ as used herein is $Ar^4$—$C_pH_{2p}$— there are included, for example, benzyl, p-tolyl, o-tolyl, m-tolyl, p-methylbenzyl, 2,4-dimethylbenzyl, phenethyl, p-methylphenethyl, 3-(m-ethylphenyl)butyl, p-methoxybenzyl, p-ethoxyphenethyl, 3-(m-isobutoxyphenyl)butyl, 3,4-dimethoxybenzyl, 3,4,5-trimethoxybenzyl, 2,4-dimethoxyphenethyl, and the like.

When $Z^1$ and $Z^2$ in the formulas herein are alkoxy there are included, for example, methoxy, ethoxy, propoxy, isopropoxy, tert-butoxy, amyloxy, 3-methylpentoxy, hexoxy, and the like.

when $Z^1$ and $Z^2$ in the formulas herein are alkenyloxy there are included, for example, allyloxy, 2-methylpropenl-yloxy, crotonyloxy, 3-methylbuten-1-yloxy, hexen-5-yloxy, and the like.

When $R^1$, $R^2$, and $R^3$ in the formulas herein are alkyl there are included methyl, ethyl, propyl, isopropyl, butyl, isobutyl, and tert-butyl. The symbol An as used herein is the anion of a strong organic or inorganic acid, for instance a halide, e.g. a chloride or bromide, or an arylsulfonate, e.g. a tosylate.

Due to the presence of the basic amino grouping, the free base forms represented by Formulas I, II, III, IV, V, and VI above react with organic and inorganic acids to form acid-addition salts. The acid-addition salt forms are prepared from any organic or inorganic acid. They are obtained in conventional fashion, for instance either by direct mixing of the base with the acid or, when this is not appropriate, by dissolving either or both of the base and the acid separately in water or an organic solvent and mixing the two solutions, or by dissolving both the base and the acid together in a solvent. The resulting acid addition salt is isolated by filtration, if it is insoluble in the reaction medium, or by evaporation of the reaction medium to leave the acid-addition salt as a residue. The acid moieties or anions in these salt forms are in themselves neither novel nor critical and therefore can be any acid anion or acid-like substance capable of salt formation with the base.

Representative acids for the formation of the acid-addition salts include formic acid, acetic acid, isobutyric acid, alpha-mercaptopropionic acid, trifluoroacetic acid, malic acid, fumaric acid, succinic acid, succinamic acid, tannic acid, glutamic acid, tartaric acid, oxalic acid, pyromucic acid, citric acid, lactic acid, glycolic acid, gluconic acid, saccharic acid, ascorbic acid, penicillin, benzoic acid, phthalic acid, salicyclic acid, 3,5-dinitrobenzoic acid, anthranilic acid, cholic acid, 2-pyridinecarboxylic acid, pamoic acid, 3-hydroxy-2-naphthoic acid, picric acid, quinic acid, tropic acid, 3-indoleacetic acid, barbituric acid, sulfamic acid, methanesulfonic acid, ethanesulfonic acid, isethionic acid, benzenesulfonic acid, p-toluenesulfonic acid, butylarsonic acid, methanephosphonic acid, acidic resins, hydrofluoric acid, hydrochloric acid, hydrobromic acid, hydriodic acid, perchloric acid, nitric acid, sulfuric acid, phosphoric acid, arsenic acid, and the like.

All of the acid-addition salts are useful as sources of the free base form, by reaction with an inorganic base. It will thus be appreciated that if one or more of the characteristics, such as solubility, molecular weight, physical appearance, toxicity, or the like of a given base or acid-addition salt thereof render that form unsuitable for the purpose at hand, it can be readily converted to another, more suitable form. For pharmaceutical purposes, acid-addition salts of relatively non-toxic, pharmaceutically-acceptable acids, for example hydrochloric acid, lactic acid, tartaric acid, and the like, are of course employed.

The compounds of this invention can exist in stereochemically isomeric forms, that is, optical isomers and geometric isomers. If desired, the isolation or the production of a particular stereochemical form can be accomplished by application of the general principles known in the prior art. In the nomenclature employed for the compounds herein, "ax" stands for axial and "eq" for equatorial, and the configurations are given with reference to the hydroaromatic ring. Thus, the 6(eq),11(ax) compounds are in the cis configuration, whereas the 6(eq),11(eq) compounds are in the trans configuration.

The compounds of Formula I and the acid-addition salts thereof are useful as depressants of the central nervous system, and more particularly are useful as analgesics and as antagonists of strong analgesics such as meperidine and morphine. These compounds of this invention can be administered in the same manner as known analgesics and antagonists of strong analgesics, i.e. parenterally or orally in any of the conventional pharmaceutical forms, as for instance solutions, suspensions, tablets, capsules, and the like. The ester species wherein Z is acyloxy are used when it is desired to have prolonged activity.

As will be seen hereinbelow, many of the species of Formula I are readily interconvertible by simple and well-known reactions such as reduction, oxidation, hydrolysis, esterification, N-acylation, etherification, and the like, so that they are also useful as intermediates for each other.

The compounds of Formulas II, III, and VI and the acid-addition salts thereof are useful as intermediates for the preparation of the compounds of Formula I. Moreover, many species of these intermediate compounds, for instance the species of Formula II wherein $Z^1$ is methoxy and the species of Formula VI wherein $Z^2$ is hydroxy, acyloxy, or methoxy, are also useful as analgesics and as antagonists of strong analgesics but generally have considerably less activity than the corresponding compounds of Formula I. After protecting any hydroxyl groups by esterification or etherification, the N-methyl compounds of Formula III can be N-demethylated by reacting first with cyanogen bromide and then hydrolyzing with dilute acid, or reducing with lithium aluminum hydride, thereby producing the corresponding nor-bases.

The compounds of Formula IV and V are useful as characterizing derivatives and, in the case of the N-carbalkoxy compounds of formula IV and the compounds of Formula V in differentiation of the 1(eq)-hydroxy compounds of Formula VI, which can be used as indicated to produce the oxazolone compounds of Formula V, from the 1(ax)-hydroxy compounds, which cannot be so used.

The manner and process of making and using the invention, and the best mode contemplated by the inventor of carrying out this invention, will now be described so as to enable any person skilled in the art to which it pertains to make and use the same.

Generally speaking, the compounds of Formulas I, II, and III of this invention are conveniently obtained by carrying out a suitable N-alkylation of the corresponding nor-bases (i.e. >N-H compounds) of Formula VI to introduce the desired N-substituent (i.e. Q or $CH_3$) by either a direct or indirect procedure. Thus, in a direct alkylation in accordance with the first process aspect of this invention, by reacting 1,2,3,4,5,6-hexahydro-1-($Y^1$) -1-($Y^2$)-8-($Z^2$)-6-($R^1$)-11-($R^2$)-2,6-methano-3-benzazocine with an alkylating agent having the formula $Q^3$-An in the presence of an acid-absorbing medium there is obtained 1,2,3,4,5,6-hexahydrol-($Y^1$)-1-($Y^2$)-3-($Q^3$)-8-($Z^2$)-6-($R^1$)-11-($R^2$)-2,6-methano-3-benzazocine. The group $Q^3$ does not include species wherein $Ar^2$ is aminophenyl but these are readily obtained through reduction of the nitrophenyl species. The acid-absorbing medium in this aklylation is conveniently an alkali metal bicarbonate, for instance sodium bicarbonate. Ordinarily it is prefereble to use a suitable reaction medium, such as a lower alkanol, for instance methanol or ethanol, or an N,N-(di-lower alkyl)-lower alkanamide, for instance N,N-dimethylformamide or N,N-dimethylacetamide.

When it is desired to introduce an N-methyl group, instead of using the above procedure, alternatively the starting 1,2,3,4,5,6-hexahydro-1-($Y^1$)-1-($Y^2$)-8-($Z^2$)-6-($R^{11}$)-11-($R^2$)-2,6-methano-3-benzazocine can be reductively formylated either by treatment with formaldehyde under conditions of catalytic hydrogenation or by treatment with a mixture of concentrated formalin solution and formic acid.

In some instances it is convenient to effect the desired N-alkylation by an indirect procedure utilizing in combination the fifth and sixth process aspects of this invention. Thus, in an initial step 1,2,3,4,5,6-hexahydro-1-($Y^1$)-1-($Y^2$)-8-($Z^2$)-6-($R^1$)-11-($R^2$)-2,6-methano-3-benzazocine is N-acylated by treatment with an active acylating form, such as an acid halide, acid anhydride, or mixed anhydride of an acid having the formula $Q^7$-COOH to yield an amide, 1,2,3,4,5,6-hexahydro-1-($Y^4$)-1-($Y^2$)-3-($Q^7$-CO-)-8-($Z^4$)-6-($R^1$)-11-($R^2$)-2,6-methano-3-benzazocine. Then in a second step (preceded if desired by reduction of any nitro group in $Q^7$ to amino) reducing the amide, 1,2,3,4,5,6-hexahydro-3-($Q^2$-CO-)-1-($Y^5$)-1-($Y^2$)-8-($Z^5$)-6-($R^1$)-11-($R^2$)-2,6-methano-3-benzazocine, with a reducing agent, such as lithium aluminum hydride, effective to reduce the carbonyl of the N-acyl group to a methylene group (i.e. —$CH_2$—) without affecting any ethylenic linkages, thereby yielding 1,2,3,4,5,6-hexahydro-1-hydroxy-1-($Y^2$)-3-($Q^8$-$CH_2$-)-8-($Z^5$)-6-($R^1$)-11-($R^2$)-2,6-methano-3-benzazocine. Any ester groups which are present in the starting 1,2,3,4,5,6-hexahydro-1-($Y^1$)-1-($Y^2$)-8-($Z^2$)-6-($R^1$)-11-($R^2$)-2,6-methano-3-benzazocine at either or both of the 8— and 1 —positions, or which are formed by esterification of hydroxyl groups at either or both of the 8— or 1 —positions by the N-acylation conditions of the first step, are converted to hydroxyl groups in the reduction step. Also, in any compounds containing a nitrophenyl moiety this will be reduced to aminophenyl. When appropriate, these hydroxyl groups can then of course be re-esterified inn conventional fashion to introduce any desired acyloxy group.

When the starting material for the initial step in this indirect alkylation procedure is a 1-oxo compound, viz. 1,2,3,4,5,6-hexahydro-1-oxo-8-($Z^2$)-6-($R^1$) ʰ11-($R^2$)-2,6-methano-3-benzazocine, and it is desired to preserve the 1-oxo group in the reduction step, so as to obtain 1,2,3,4,5,6-hexahydro-1-oxo-3-($Q^8$-$CH_2$-)-8-($Z^5$)-6-($R^1$)-11-($R^2$)-2,6-methano-3-benzazocine, the 1-oxo group is protected in conventional fashion by conversion to a ketal function prior to the reduction. Thus, for instance the starting material for either the first or second steps is interacted with a lower alkanol; or with a lower 1,2 or 1,3-alkylene glycol to form a cyclic ketal, for example the ethylenedioxy derivative. After the reduction the ketal is readily hydrolyzed with acid to regenerate the oxo group.

The 1,2,3,4,5,6-hexahydro-1-($Y^1$)-1-($Y^2$)-8-($Z^2$)-6-($R^1$)-11-($R^2$)-2,6-methano-3-benzazocines (Formula VI) required as starting materials for the above-described alkylation procedures are conveniently obtained starting with 1,2,3,4,5,6-hexahydro-8-($Z^3$)-6-($R^1$)-11-($R^2$)-2,6-methano-3-benzazocines (Formula VIII wherein $Q^4$ is hydrogen) a known class of compounds readily obtained by procedures well-known in the prior art. Oxidation of these latter compounds (Formula VIII) with chromium(VI) in acid medium in accordance with the above-mentioned second process aspect of this invention results in introduction of an oxo group at the 1-position to yield 1,2,3,4,5,6-hexahydro-1-oxo-8-($Z^3$)-6-($R^1$)-11-($R^2$)-2,6-methano-3-benzazocines (Formula IX wherein $Q^4$ is hydrogen). These species afford ready access to the further members of the desired 1,2,3,4,5,6-hexahydro-1-($Y^1$)-1-($Y^2$)-8-($Z^2$)-6-($R^1$)-11-($R^2$)-2,6-methano-3-benzazocine starting materials. Thus, for example, by heating the 1,2,3,4,5,6-hexahydro-1-oxo-8-alkoxy-6-($R^1$)-11-($R^2$)-2,6-methano-3-benzazocines with concentrated hydriodic acid or hydrobromic acid there are obtained 1,2,3,4,5,6-hexahydro-1-oxo-8-hydroxy-6-($R^1$)-11-($R^2$)-2,6-methano-3-benzazocines. These latter can then if desired be O-acylated, by conventional methods for esterification of phenols, to introduce the various acyloxy groups defined by $Y^1$, which are of course also embraced by Z, thus yielding the desired corresponding 8-acyloxy esters; or, alternatively, if desired the 8-hydroxy group can be appropriately etherified by conventional methods for etherification of phenols to convert it to an 8-alkenyloxy group having 3–6 carbon atoms, or the 8-difluoromethoxy group, or the 8-trifluoromethoxy group. As indicated more particularly hereinbelow, these 1,2,3,4,5,6-hexahydro-1-oxo-8-($Z^2$)-6-($R^1$)-11-($R^2$)-2,6-methano-3-benzazocines can be used as starting materials in the reduction and Grignard reactions of the third and fourth process aspects, respectively, of this invention.

Instead of using the above-described N-alkylation procedures to produce the desired N-substituted compounds of Formulas I, II, and III from the corresponding nor-bases (Formula VI), the N-substituent can if desired be introduced at an earlier stage in the synthetic sequence. Thus, in the second, third, and fourth process aspects the starting materials in the respective oxidation, reduction, and Grignard reactions can be either nor-bases or the corresponding compounds bearing N-(Q or methyl) substituents.

In accordance with the second process aspect of this invention, 1,2,3,4,5,6-hexahydro-3-($Q^4$)-8-($Z^3$)-6-($R^1$)-11-($R^2$)-2,6-methano-3-benzazocines (Formula VIII) are oxidized with chromium(VI) in acid medium to yield 1,2,3,4,5,6-hexahydro-1-oxo-3-($Q^4$)-8-($Z^3$)-6-($R^1$)-11-($R^2$)-2,6-methano-3-benzazocines (Formula IX). (The group $Q^4$ does not include benzyl or substituted benzyl because these are attacked by the oxidizing agent.) The oxidizing medium for this reaction is conveniently prepared by dissolving chromium trioxide in a solution of an inorganic acid such as sulfuric acid, hydrochloric acid, phosphoric acid, or the like, or in acetic anhydride, trichloroacetic acid or other suitable organic acid, or mixtures thereof. In these media, the chromium(VI) species is chromic acid or a chromyl compound, i.e., chromyl chloride, chromyl acetate, chromyl sulfate, or the like, or mixtures thereof as the case may be. The oxidation rate is dependent on the structure of the starting material and the particular species of chromium (VI) employed but, generally speaking, satisfactory reaction rates result at temperatures in the approximate range 20°–100°C.

In accordance with the third process aspect of this invention, 1,2,3,4,5,6-hexahydro-1-oxo-3-($Q^5$)-8-($Z^2$)-6-($R^1$)-11-($R^2$)-2,6-methano-3-benzazocine is reduced by treatment with any suitable reducing means effective to convert the 1-oxo group to a 1-hydroxyl group without affecting any ethylenic linkages which are present. For instance, aluminum hydride, lithium aluminum hydride, lithium borohydride, lithium trimethoxyaluminum hydride, and, when ester or cyano groups are present and it is desired to leave these intact, sodium borohydride or lithium tri-tert-butoxyaluminum hydride generally afford satisfactory results. When no aliphatic ethylenic linkages are present, or when it is desired to reduce such linkages, catalytic hydrogenation can be employed.

In accordance with the fourth process aspect of this invention, those 1,2,3,4,5,6-hexahydro-1-oxo-3-($Q^6$)-8-(Z)-6-($R^1$)-11-($R^2$)-dimethyl-2,6-methano-3-benzazocines having no groups other than the 1-oxo group which are susceptible to reaction with Grignard reagents, viz. the 1,2,3,4,5,6-hexahydro-1-oxo-3-($Q^6$)-8-($Z^3$)-6-($R^1$)-11-($R^2$)-2,6-methano-3-benzazocines, can be reacted in a Grignard reaction with a Grignard reagent having the formula $Y^3$-Mg-halogen to yield 1,2,3,4,5,6-hexahydro-1-hydroxy-1-($Y^3$)-3-($Q^6$)-8-($Z^3$)-6-($R^1$)-11-($R^2$)-2,6-methano-3-benzazocines. This reaction is carried out under the usual Grignard reaction conditions, i.e. in an anhydrous diethyl ether medium, the initially-obtained Grignard adduct being decomposed by treatment with weak aqueous acid, for instance aqueous ammonium chloride solution, to release the desired tertiary carbinol product.

The 3a,4,5,9b-tetrahydro-7-($Z^2$)-9b-($Y^2$)-4-($R^2$)-5-($R^1$)-3,5-ethanonaphth[2,1-d]oxozol-2(3H)-ones (Formula V) are obtained in accordance with either of the seventh or the eighth process aspects of this invention. Thus, in the former of these two methods phosgene is interacted with 1,2,3,4,5,6-hexahydro-1-hydroxy-1-($Y^2$)-8-($Z^2$)-6-($R^1$)-11-($R^2$)-2,6-methano-3-benzazocine, conveniently by bubbling phosgene gas through a solution of the benzazocine in a suitable solvent and preferably in the presence of an acid-acceptor such as a tertiary amine; nd in the latter method 1,2,3,4,5,6-hexahydro-1-hydroxy-1-($Y^2$)-3-(carbalkoxy)-8-($Z^2$)-6-($R^1$)11-($R^2$)-2,6-methano-3-benzazocine is heated in the presence of a catalytic amount of alkoxide ion, provided for instance by a metal alkoxide, e.g. aluminum isopropylate.

The 1,2,3,4,5,6-hexahydro-1-hydroxy-1-($Y^2$)-3-(carbalkoxy)-8-($Z^2$)-6-($R^1$)-11-($R^2$)-2,6-methano-3-benzazocines (Formula IV wherein $Q^1$ is carbalkoxy) required as starting materials in the latter method above and the corresponding 3-(carbobenzyloxy) compounds (Formula IV wherein $Q^1$ is carbobenzyloxy) are conveniently obtained by reacting 1,2,3,4,5,6-hexahydro-1-hydroxy-1-($Y^2$)-8-($Z^2$)-6-($R^1$)-11-($R^2$)-2,6-methano-3-benzazocine with a alkyl haloformate wherein alkyl containing 1–6 carbon atoms, for instance ethyl chloroformate, or with a benzyl haloformate, for instance p-methoxybenzyl chloroformate, respectively, in the presence of an acid-binding agent, for instance sodium hydroxide, preferably at low temperature.

The compounds of Formula IV wherein $Q^1$ is N-(carbalkoxy)aminoacetyl or N-(carbobenzyloxy)aminoacetyl are conveniently obtained using the mixed anhydride of an N-(carbalkoxy or carbobenzyloxy)aminoacetic with an alkyl acid carbonate, this mixed anhydride being interacted with 1,2,3,4,5,6-hexahydro-1-oxo-8-($Z^2$)-6-($R^1$)-11-($R^2$)-2,6-methano-3-benzazocine. The mixed anhydride is prepared in conventional fashion by interacting an N-(carbalkoxy or carbobenzyloxy)aminoacetic acid with an alkyl haloformate, for instance isobutyl chloroformate, at low temperature in the presence of a tertiary amine, for instance triethylamine.

The structures of the compounds of this invention were established by the modes of synthesis, by elementary analysis, and by ultraviolet, infrared, and nuclear magnetic resonance spectra. The course of the reactions and homogeneity of the products were ascertained by thin layer chromatography.

The invention is illustrated by the following examples without, however, being limited thereto. The melting points are uncorrected except where otherwise indicated.

EXAMPLE 1

A.

A mixture of 9.6 g. of 1,2,3,4,5,6-hexahydro-1-oxo-8-hydroxy-6(eq),11(ax)-dimethyl-2,6-methano-3-benzazocine, 5.6 g. of cyclopropylmethyl bromide, 3.5 g. of sodium bicarbonate, and 100 ml. of N,N-dimethylformamide was stirred and refluxed for 2 hours, and then the reaction mixture was concentrated under reduced pressure. The resulting residue was triturated with water, cooled in ice, and filtered. The white crystalline solid thus collected was washed with water and methyl alcohol and dried. This product, which weighed 8.3 g., was 1,2,3,4,5,6-hexahydro-1-oxo-3-cyclopropylmethyl-9-hydroxy-6(eq),11(ax)-dimethyl-2,6-methano-3-benzazocine. (After recrystallization from methyl alcohol, this compound was a white crystalline solid which melted at 249°–252°C.) This base was treated with ethanolic hydrogen chloride to convert it to the hydrochloride, a white crystalline solid which, after recrystallization from ethyl alcohol, melted at 272°–276°C. By treatment of the base with methanesulfonic acid there was obtained the methanesulfonate as a white solid which melted at 257°–258°C.

B.

Proceeding as above in part A but using 1,2,3,4,5,6-hexahydro-1-oxo-8-hydroxy-2,6-methano-3-benzazocine, 1,2,3,4,5,6-hexahydro-1-oxo-8-hydroxy-6(eq)- methyl-2,6-methano-3-benzazocine, and 1,2,3,4,5,6-hexahydro-1-oxo-8-hydroxy-6(eq)-butyl-11(ax)-methyl-2,6-methano-3-benzazocine, respectively, instead of the 6(eq), 11 (ax)-dimethyl (eg), there are obtained the following products which by esterification with the appropriate acid chloride, for instance as illustrated below in Examples 2–13, can be converted to the indicated respective esters:

1,2,3,4,5,6-hexahydro-1-oxo-3-cyclopropylmethyl-8-hydroxy-2,6-methano-3-benzazocine and the corresponding 8-m-toluyloxy ester;

1,2,3,4,5,6-hexahydro-1-oxo-3-cyclopropylmethyl-8-hydroxy-6(eq)-methyl-2,6-methano-3-benzazocine and the corresponding 8-acetoxy ester; and 1,2,3,4,5,6-hexahydro-1-oxo-3-cyclopropylmethyl-8-hydroxy-6(eq)-butyl-11(ax)-methyl-2,6-methano-3-benzazocine and the corresponding 8-m-anisoyloxy ester.

C.

Proceeding as in part A, but using 1-cyclohexenylmethyl bromide, 4-(2-cyclopentenyl)butyl bromide, and 3,4-dimethyl-3-cyclohexenyl bromide instead of cyclopropylmethyl bromide, there are obtained respectively:

1,2,3,4,5,6-hexahydro-1-oxo-3-(1-cyclohexenylmethyl)-8-hydroxy-6(eq),11(ax)-dimethyl-2,6-methano-3-benzazocine;

1,2,3,4,5,6-hexahydro-1-oxo-3-[4-(2-cyclopentenyl)butyl]-8-hydroxy-6(eq),11(ax)-dimethyl-2,6-methano-3-benzazocine; and 1,2,3,4,5,6-hexahydro-1-oxo-3-(3,4-dimethyl-3-cyclohexenyl)-8-hydroxy-6(eq),11(ax)-dimethyl-2,6-methano-3-benzazocine.

EXAMPLE 2

A mixture of 10.0 g. of 1,2,3,4,5,6-hexahydro-1-oxo-3-cyclopropylmethyl-8-hydroxy-6(eq),11(ax)-dimethyl-2,6-methano-3-benzazocine and 100 ml. of acetic anhydride was heated and stirred on a steam-bath for 3 hours. The resulting reaction mixture was concentrated and the residue was dissolved in 50 ml. of ethyl acetate and treated with ethereal hydrogen chloride solution. From this mixture there was recovered 11.3 g. of solid which when recrystallized from boiling ethyl acetate yielded 7.6 g. of 1,2,3,4,5,6-hexahydro-1-oxo-3-cyclopropylmethyl-8-acetoxy-6(eq),11(ax)-dimethyl-2,6-methano-3-benzazocine hydrochloride as a white solid which melted at 195°–197°C.

EXAMPLE 3

A mixture of 10.0 g. of 1,2,3,4,5,6-hexahydro-1-oxo-3-cyclopropylmethyl-8-hydroxy-6(eq),11(ax)-dimethyl-2,6-methano-3-benzazocine and 100 ml. of propionic anhydride was heated and stirred on a steam-bath for 3½ hours. The reaction mixture was concentrated under reduced pressure, and the resulting residue was dissolved in 50 ml. of ethyl acetate and treated with ethereal hydrogen chloride solution. From the resulting mixture there was recovered 12.4 g. of solid which when recrystallized from ethyl acetate yielded 8.5 g. of 1,2,3,4,5,6-hexahydro-1-oxo-3-cyclopropylmethyl-8-propionyloxy-6(eq),11(ax)-dimethyl-2,6-methano-3-benzazocine hydrochloride as a white solid which melted at 187°–188°C.

EXAMPLE 4

To 11.2 g. of 1,2,3,4,5,6-hexahydro-1-oxo-3-cyclopropylmethyl-8-hydroxy-6(eq),11(ax)-dimethyl-2,6-methano-3-benzazocine in 120 ml. of N,N-dimethylformamide there was added 2.4 g. of sodium methoxide. After distilling off 40 ml. of solvent, the mixture was cooled to room temperature, 4.85 g. of butyryl chloride was added dropwise, and the mixture was stirred for 1½ hours and then allowed to stand overnight. The reaction mixture was concentrated under reduced pressure, the resulting residue was dissolved in 200 ml. of diethyl ether, and the ether solution was shaken quickly with 100 ml. of water. The ether solution was separated, dried, and filtered and the ether was evaporated from the filtrate. The residue thus obtained was dissolved in 50 ml. of ethyl acetate, ethereal hydrogen chloride solution was added, and the solution was cooled. The 8.9 g. of solid which separated in two crops was recrystallized from ethyl acetate to yield 6.3 g. of 1,2,3,4,5,6-hexahydro-1-oxo-3-cyclopropylmethyl-8-butyryloxy-6(eq),11(ax)-dimethyl-2,6-methano-3 -benzazocine hydrochloride as a white solid which melted at 195°–197°C.

EXAMPLE 5

Proceeding in a manner similar to that described in Example 4 above, 11.2 g. of 1,2,3,4,5,6-hexahydro-1-oxo-3-cyclopropylmethyl-8-hydroxy-6(eq),11(ax)-dimethyl-2,6-methano-3-benzazocine in 100 ml. of N,N-dimethylformamide was treated with 2.4 g. of sodium methoxide. The resulting product was reacted with 5.3 g. of pivalyl chloride to yield 1,2,3,4,5,6-hexahydro-1-oxo-3-cyclopropylmethyl-8-pivalyloxy-6(eq),11(ax)-dimethyl-2,6-methano-3-benzazocine. This base was converted by treatment with ethereal hydrogen chloride solution to 5.9 g. of the hydrochloride, a white solid which melted at 194°–196°C.

EXAMPLE 6

Proceeding in a manner similar to that described in Example 4 above, 11.2 g. of 1,2,3,4,5,6-hexahydro-1-oxo-3-cyclopropylmethyl-8-hydroxy-6(eq),11(ax)-dimethyl-2,6-methano-3-benzazocine in 100 ml. of N,N-dimethylformamide was treated with 2.4 g. of sodium methoxide. The resulting product was reacted with 4.8 g. of isobutyryl chloride to yield 1,2,3,4,5,6-hexahydro-1-oxo-3-cyclopropylmethyl-8-isobutyryloxy-6(eq),11(ax)-dimethyl-2,6-methano-3-benzazocine. This base was converted by treatment with ethereal hydrogen chloride solution to 7.8 g. of the hydrochloride, a white solid which melted at 197°–200°C.

EXAMPLE 7

Proceeding in a manner similar to that described in Example 4 above, 11.2 g. of 1,2,3,4,5,6-hexahydro-1-oxo-3-cyclopropylmethyl-8-hydroxy-6(eq),11(ax)-dimethyl-2,6-methano-3-benzazocine in 100 ml. of N,N-dimethylfromamide was treated with 2.4 g. of sodium -methoxide. The resulting product was reacted with 5.3 g. of isovaleryl chloride to yield 1,2,3,4,5,6-hexahydro-1-oxo-3-cyclopropylmethyl-8-isovaleryloxy-6(eq),11(ax)-dimethyl-2,6-methano-3-benzazocine which was converted by treatment with ethereal hydrogen chloride solution to 6.9 g. of the hydrochloride, a white solid which melted at 182°–185°C.

EXAMPLE 8

A.

Proceeding in a manner similar to that described in Example 4 above, 11.2 g. of 1,2,3,4,5,6-hexahydro-1- oxo-3-cyclopropylmethyl-8-hydroxy-6(eq),11(ax)-dimethyl-2,6-methano-3-benzazocine in 100 ml. of N,N-dimethylformamide was treated with 2.4 g. of sodium methoxide. The resulting product was reacted with 5.9 g. of 3,3-dimethylbutanoyl chloride to yield 1,2,3,4,5,6-hexahydro-1-oxo-3-cyclopropylmethyl-8-(3,3-dimethylbutanoyloxy)-6(eq),11(ax)-dimethyl-2,6-methano-3-benzazocine. This base was converted by treatment with ethereal hydrogen chloride solution to 9.8 g. of the hydrochloride, a white solid which melted at 185°–187°C.

B.

Proceeding in a fashion similar to that described in part A and interacting 1,2,3,4,5,6-hexahydro-1-oxo-3-cyclopropylmethyl- 8-hydroxy-2,6-methano-3-benzazocine with the appropriate acid chloride there can be obtained:

1,2,3,4,5,6-hexahydro-1-oxo-3-cyclopropylmethyl-8-stearoyloxy-6(eq),11(ax)-dimethyl-2,6-methano-3-benzazocine;

1,2,3,4,5,6-hexahydro-1-oxo-3-cyclopropylmethyl-8-(3,6-octadienoyloxy)-6(eq),11(ax)-dimethyl-2,6-methano-3-benzazocine;

1,2,3,4,5,6-hexahydro-1-oxo-3-cyclopropylmethyl-8-methylcarbonato-6(eq),11(ax)-dimethyl-2,6-methano-3-benzazocine;

1,2,3,4,5,6-hexahydro-1-oxo-3-cyclopropylmethyl-8-carbamyloxy-6(eq),11(ax)-dimethyl-2,6-methano-3-benzazocine; and 1,2,3,4,5,6-hexahydro-1-oxo-3-cyclopropylmethyl-8-diethylaminocarbonyloxy-6(eq),11(ax)-dimethyl-2,6-methano-3-benzazocine.

EXAMPLE 9

Proceeding in a manner similar to that described in Example 4 above, 11.2 g. of 1,2,3,4,5,6-hexahydro-1-oxo-3-cyclopropylmethyl-8-hydroxy-6(eq),11(ax)-dimethyl-2,6-methano-3-benzazocine in 100 ml. of N,N-dimethylformamide was treated with 2.4 g. of sodium methoxide. The resulting product was reacted with 6.2 g. of benzoyl chloride to yield 1,2,3,4,5,6-hexahydro-1-oxo-3-cyclopropylmethyl-8-benzoyloxy-6(eq),11(ax)-dimethyl-2,6-methano-3-benzazocine. This base was converted by treatment with ethereal hydrogen chloride solution to 5.3 g. of the hydrochloride, a white solid which melted at 190°–191°C.

EXAMPLE 10

Proceeding in a manner similar to that described in Example 4 above, 11.2 g. of 1,2,3,4,5,6-hexahydro-1-oxo-3-cyclopropylmethyl-8-hydroxy-6(eq),11(ax)-dimethyl-2,6-methano-3-benzazocine in 120 ml. of N,N-dimethylformamide was treated with 2.4 g. of sodium methoxide. The resulting product was reacted with 7.5 g. of p-anisoyl chloride to yield 1,2,3,4,5,6-hexahydro-1-oxo-3-cyclopropylmethyl-8-(p-anisoyloxy)-6(eq),11(ax)-dimethyl-2,6-methano-3-benzazocine. This base was converted by treatment with ethereal hydrogen chloride solution to 11.3 g. of the hydrochloride, a white solid which melted at 200°–202°C.

EXAMPLE 11

When m-anisoyl chloride was substituted for the p-anisoyl chloride in the procedure described in Example 10, the product obtained was 5.0 g. of 1,2,3,4,5,6-1-oxo-3-cyclopropylmethyl-8-(m-anisoyloxy)-6(eq),1-1(ax)-dimethyl-2,6-methano-3-benzazocine hydrochloride, a white solid which melted at 159°–161°C.

EXAMPLE 12

Proceeding in a manner similar to that described in Example 4 above, 11.2 g. of 1,2,3,4,5,6-hexahydro-1-oxo-3-cyclopropylmethyl-8-hydroxy-6(eq),11(ax)-dimethyl-2,6-methano-3-benzazocine in 120 ml. of N,N-dimethylformamide was treated with 2.4 g. of sodium methoxide. The resulting product was reacted with 6.8 g. of p-toluyl chloride to yield 1,2,3,4,5,6-hexahydro-1-oxo-3-cyclopropylmethyl-8-(p-toluyloxy)-6(eq),11(ax)-dimethyl-2,6-methano-3-benzazocine. This base was converted by treatment with ethereal hydrogen chloride solution to 7.2 g. of the hydrochloride hemi(ethyl acetate), a white solid which melted at 201°–203°C.

EXAMPLE 13

A.

Proceeding in a manner similar to that described in Example 4 above, 11.2 g. of 1,2,3,4,5,6-hexahydro-1-oxo-3-cyclopropylmethyl-8-hydroxy-6(eq),11(ax)-dimethyl-2,6-methano-3-benzazocine in 120 ml. of N,N-dimethylformamide was treated with a 2.4 g. of sodium methoxide. The resulting product was reacted with 9.15 g. of p-trifluoromethylbenzoyl chloride to yield 1,2,3,4,5,6-hexahydro-1-oxo-3-cyclopropylmethyl-8-(p-trifluoromethylbenzoyloxy)-6(eq),11(ax)-dimethyl-2,6 -methano-3-benzazocine. This base was converted by treatment with ethereal hydrogen chloride solution to 9.7 g. of the hydrochloride, a white solid which melted at 226°–229°C.

B.

Proceeding in a fashion similar to that in part A and interacting 1,2,3,4,5,6-hexahydro-1-oxo-3-cyclopropylmethyl-8-hydroxy-2,6-methano-3-benzazocine with the appropriate acid chloride there can be obtained:

1,2,3,4,5,6-hexahydro-1-oxo-3-cyclopropylmethyl-8-[3-(p-fluorophenyl)propionyloxy]-6(eq),11(ax)-dimethyl-2,6-methano-3-benzazocine;

1,2,3,4,5,6-hexahydro-1-oxo-3-cyclopropylmethyl-8-(p-dimethylaminobenzoyloxy)-6(eq),11(ax)-dimethyl-2,6-methano-3-benzazocine;

1,2,3,4,5,6-hexahydro-1-oxo-3-cyclopropylmethyl-8-(m-acetamidobenzoyloxy)-6(eq),11(ax)-dimethyl-2,6-methano-3-benzazocine;

1,2,3,4,5,6-hexahydro-1-oxo-3-cyclopropylmethyl-8-phenoxyacetoxy-6(eq),11(ax)-dimethyl-2,6-methano-3-benzazocine;

1,2,3,4,5,6-hexahydro-1-oxo-3-cyclopropylmethyl-8-(1-naphthalenecarbonyloxy)-6(eq),11(ax)-dimethyl-2,6-methano-3-benzazocine;

1,2,3,4,5,6-hexahydro-1-oxo-3-cyclopropylmethyl-8-nicotinoyloxy-6(eq),11(ax)-dimethyl-2,6-methano-3-benzazocine; and 1,2,3,4,5,6-hexahydro-1-oxo-3-cyclopropylmethyl-8-cyclopropanecarbonyloxy-6(eq),11(ax)-dimethyl-2,6-methano-3-benzazocine.

EXAMPLE 14

Proceeding in a manner similar to that described above in part A of Example 1, 24.5 g. of 1,2,3,4,5,6-hexahydro-1-oxo-8-methoxy-6(eq),11(ax)-dimethyl-2,6-methano-3-benzazocine was interacted with 9.0 g. of cyclopropylmethyl chloride in the presence of 8.4 g. of sodium bicarbonate and 250 ml. of N,N-dimethylformamide to yield 25 g. of crude 1,2,3,4,5,6-hexahydro-1-oxo-3-cyclopropylmethyl-8-methoxy-6(eq),11(ax)-dimethyl-2,6-methano-3-benzazocine which was converted to 22.0 g. of the crude base hydrochloride, m.p. 187°–190°C. Two recrystallizations of this salt from ethyl alcohol-diethyl ether yielded 12.2 g. of 1,2,3,4,5,6-hexahydro-1-oxo-3-cyclopropylmethyl-8-methoxy-6(eq),11(ax)-dimethyl-2,6-methano-3-benzazocine hydrochloride as a white solid which melted at 192°–193°C.

EXAMPLE 15

A mixture of 13.4 g. of 1,2,3,4,5,6-hexahydro-1-oxo-6(eq),11(ax)-dimethyl-2,6-methano-3-benzazocine, 9.3 g. of cyclopropylmethyl bromide, 5.3 g. of sodium bicarbonate, and 150 ml. of N,N-dimethylformamide was stirred and refluxed for 2 hours. The reaction mixture was then concentrated under reduced pressure and the resulting residue was partitioned between diethyl ether and water. When concentrated ammonium hydroxide was added, crude 1,2,3,4,5,6-hexahydro-1-oxo-3-cyclopropylmethyl-6(eq),11(ax)-dimethyl-2,6-methano-3-benzazocine separated as an oil which crystallized on standing. The mixture was shaken to dissolve the base in the ether layer and the ether layer was seprated, washed with water, dried, treated with decolorizing charcoal, and filtered. The filtrate was concentrated to yield 15.5 g. of the base which was treated with ethereal hydrogen chloride to produce the base hydrochloride. This salt was recrystallized from diethyl ether-anhydrous ethyl alcohol to yield 11.5 g. of 1,2,3,4,5,6-hexahydro-1-oxo-3-cyclopropylmethyl-6(eq),11(ax)-dimethyl-2,6-methano-3-benzazocine hydrochloride as a white solid which melted at 224°–226°C.

EXAMPLE 16

A.

A mixture of 9.24 g. of 1,2,3,4,5,6-hexahydro-1-oxo-8-hydroxy-6(eq),11(ax)-dimethyl-2,6-methano-3-benzazocine, 7.48 g. of n-propyl iodide, 3.36 g. of sodium bicarbonate, and 100 ml. of N,N-dimethylformamide was stirred and refluxed for 6 ¼ hours. The reaction mixture was concentrated under reduced pressure and then water and diethyl ether were added. Some of the residue failed to dissolve. The mixture was filtered to collect the crystalline solid which separated from solution. The ether layer and the aqueous layer of the filtrate were separated and the ether layer was evaporated under reduced pressure to yield a further crop of solid which was collected by filtration and washed with water. The two crops of crystalline solid were combined with the undissolved residue from the reaction mixture, and these combined solids were taken up in boiling ethyl alcohol and treated with decolorizing charcoal and the solution was filtered while hot. The filtrate was cooled and the solid which separated from solution was collected on a filter, washed with cold ethyl alcohol, and dried under reduced pressure at 50°C. for 3 hours. There was thus obtained 8.0 g. of solid which melted at 218°–221°C. The mother liquor from this crystallization was concentrated under reduced pressure to yield a crystalline solid which was collected on a filter, washed with cold ethyl alcohol and dried at 70°C. There was thus obtained a second crop of product weighing 1.15 g. which melted at 214°–218°C. These two crops were combined and recrystallized from ethyl alcohol and dried overnight at 70°C. There was thus obtained 7.0 g. of 1,2,3,4,5,6-hexahydro-1-oxo-3-propyl-8-hydroxy-6(eq),11(ax)-dimethyl-2,6-methano-3-benzazocine as an off-white solid which melted at 219°–222°C.

B.

Proceeding in a manner similar to that described in part A but using isooctyl bromide, benzyl bromide, phenethyl bromide, p-tolylmethyl bromide, p-methoxybenzyl bromide, 3,4-dibutoxybenzyl bromide, cis-1,3-dichloro-1-propene, cis-1,3-dibromo-1-propene, p-nitrophenethyl bromide, m-acetamidobenzyl bromide, 3-(m-hexanoylaminophenyl)-propyl bromide, p-chlorobenzyl bromide, 3,4-dimethoxyphenethyl bromide, p-fluorobenzyl bromide, m-bromophenethyl bromide, and p-trifluoromethylphenethyl bromide instead of m-propyl iodide, there are obtained, respectively:

1,2,3,4,5,6-hexahydro-1-oxo-3-isooctyl-8-hydroxy-6(eq),11(ax)-dimethyl-2,6-methano-3-benzazocine;

1,2,3,4,5,6-hexahydro-1-oxo-3-benzyl-8-hydroxy-6(eq),11(ax)-dimethyl-2,6-methano-3benzazocine;

1,2,3,4,5,6-hexahydro-1-oxo-3-phenethyl-8hydroxy-6(eq),11(ax)-dimethyl-2,6-methano-3-benzazocine;

1,2,3,4,5,6-hexahydro-1-oxo-3-(p-tolylmethyl)-8-hydroxy-6(eq),11(ax)-dimethyl-2,6-methano-3-benzazocine;

1,2,3,4,5,6-hexahydro-1-oxo-3-(p-methoxybenzyl)-8-hydroxy-6(eq),11(ax)-dimethyl-2,6-methano-3-benzazocine;

1,2,3,4,5,6-hexahydro-1-oxo-3-(3,4-dibutoxybenzyl)-8-hydroxy-6(eq),11(ax)-dimethyl-2,6-methano-3-benzazocine;

1,2,3,4,5,6-hexahydro-1-oxo-3-(cis-3-chloro-2-propenyl)-8-hydroxy-6(eq),11(ax)-dimethyl-2,6-methano-3-benzazocine;

1,2,3,4,5,6-hexahydro-1-oxo-3-(cis-3-bromo-2-propenyl)-8-hydroxy-6(eq),11(ax)-dimethyl-2,6-methano-3-benzazocine;

1,2,3,4,5,6-hexahydro-1-oxo-3-(p-nitrophenethyl)-8-hydroxy-6(eq),11(ax)-dimethyl-2,6-methano-3-benzazocine;

1,2,3,4,5,6-hexahydro-1-oxo-3-(m-acetamidobenzyl)-8-hydroxy-6(eq),11(ax)-dimethyl-2,6-methano-3-benzazocine;

1,2,3,4,5,6-hexahydro-1-oxo-3-[3-(m-hexanoylaminophenyl)propyl]-8-hydroxy-6(eq),11(ax)-dimethyl-2,6-methano-3-benzazocine;

1,2,3,4,5,6-hexahydro-1-oxo-3-(p-chlorobenzyl)-8-hydroxy-6(eq),11(ax)-dimethyl-2,6-methano-3-benzazocine;

1,2,3,4,5,6-hexahydro-1-oxo-3-(3,4-dimethoxyphenethyl)-8-hydroxy-6(eq),11(ax)-dimethyl-2,6-methano-3-benzazocine;

1,2,3,4,5,6-hexahydro-1-oxo-3-(p-fluorobenzyl)-8-hydroxy-6(eq),11(ax)-dimethyl-2,6-methano-3-benzazocine;

1,2,3,4,5,6-hexahydro-1-oxo-3-(m-bromophenthyl)-8-hydroxy-6(eq),11(ax)-dimethyl-2,6-methano-3-benzazocine; and 1,2,3,4,5,6-hexahydro-1-oxo-3-(p-trifluoromethylphenethyl)-8-hydroxy-6(eq),11(ax)-dimethyl-2,6-methano-3-benzazocine.

EXAMPLE 17

A mixture of 12.2 g. of 1,2,3,4,5,6-hexahydro-1-oxo-8-methoxy-6(eq),11(ax)-dimethyl-2,6-methano-3-benzazocine, 9.4 g. of n-propyl iodide, 4.2 g. of sodium bicarbonate, and 125 ml. of N,N-dimethylformamide was stirred and refluxed for approximately 2 hours. The reaction mixture was evaporated to dryness under reduced pressure, the resulting residue was partitioned between water and diethyl ether, and 12.9 g. of crude 1,2,3,4,5,6-hexahydro-1-oxo-3-propyl-8-methoxy-6(eq),11(ax)-dimethyl-2,6-methano-3-benzazocine was recovered from the ethereal extract thus obtained. This base was converted to the hydrochloride, a white solid which weighed 8.1 g. and melted at 223°–225°C.

EXAMPLE 18

To a stirred mixture of 5.65 g. of 1,2,3,4,5,6-hexahydro-1-oxo-8-methoxy-6(eq),11(ax)-dimethyl-2,6-methano-3-benzazocine hydrochloride, 5.0 g. of sodium bicarbonate, and 50 ml. of N,N-dimethylformamide there was added dropwise a solution of 3.7 g. of 2,2-dimethoxyethyl bromide in 25 ml. of N,N-dimethylformamide. This mixture was stirred and refluxed for 5hours. The reaction mixture was then cooled in an ice bath and filtered to remove a small amount of solid which was washed with methyl alcohol. The filtrate, including the methanolic rinse liquor, was concentrated under reduced pressure. The resulting residue was taken up in a mixture of dilute ammonium hydroxide and diethyl ether. The aqueous and etheral layers were separated and the aqueous layer was extracted with diethyl ether, and the two ether solutions were combined, washed with water, dried, treated with decolorizing charcoal, and filtered. Ethereal hydrogen chloride solution was added to the filtrate, thereby causing appearance of a crystalline solid. This solid was collected on a filter, washed with diethyl ether and dried under reduced pressure at 45°–50°C. The product thus obtained weighed 6.5 g. and melted at 173°–178°C. (dec.). This product was recrystallized twice from ethyl acetate. There was thus obtained 3.7 g. of 1,2,3,4,5,6-hexahydro-1-oxo-3-(2,2-dimethoxyethyl)-8-methoxy-6(eq),11(ax)-dimethyl-2,6-methano-3-benzazocine hydrochloride as a white solid which melted at 175°C. (dec.).

EXAMPLE 19

A mixture of 4.63 g. of 1,2,3,4,5,6-hexahydro-1-oxo-8-hydroxy-6(eq),11(ax)-dimethyl-2,6-methano-3-benzazocine, 2.5 g. of sodium bicarbonate and 50 ml. of N,N-dimethylformamide was stirred, and 2.66 g. of allyl bromide was added, using 10 ml. of N,N-dimethylformamide to rinse in the residual portion of allyl bromide. The reaction mixture was stirred for 15 minutes at room temperature and then refluxed for 1 ½ hours. The mixture was cooled and filtered and the filtrate was concentrated under reduced pressure. The resulting residue was taken up in a mixture of water and ethyl acetate, and the aqueous layer was separated and extracted with ethyl acetate. The ethyl acetate extract was combined with the ethyl acetate layer and washed with water, treated with decolorizing charcoal, and filtered. The filtrate was concentrated under reduced pressure and the crystalline residue thus obtained was washed with benzene. This product was 1,2,3,4,5,6-hexahydro-1-oxo-3-allyl-8-hydroxy-6(eq),11 (ax)-dimethyl-2,6-methano-3-benzazocine. The aqueous layer was concentrated to dryness and the residue was taken up in a mixture of water and diethyl ether. The ether layer was separated, dried, and concentrated under reduced pressure. The resulting oily residue was a second crop of the desired base. Both crops of the base were converted to the hydrochloride by treatment with ethereal hydrogen chloride. The two crops of hydrochloride (2 g.) were combined and recrystallized from isopropyl alcohol and dried overnight under reduced pressure at 60°C. There was thus obtained 1.4 g. of 1,2,3,4,5,6-hexahydro-1-oxo-3-allyl-8-hydroxy-6(eq),11(ax)-dimethyl-2,6-methano-3-benzazocine hydrochloride as a white solid which melted at 251.0°–252.0°C. (dec.)(corr.).

EXAMPLE 20

A mixture of 20 g. of 1,2,3,4,5,6-hexahydro-1-oxo-8-methoxy-6(eq),11(ax)-dimethyl-2,6-methano-3-benzazocine hydrochloride, 18 g. of sodium bicarbonate, and 150 ml. of N,N-dimethylformamide was stirred and to this mixture there was added dropwise a solution of 9.5 g. of allyl bromide in 50 ml. of N,N-dimethylformamide. After this addition was complete, the reaction mixture was refluxed for 2 hours, cooled, and filtered to collect the solid which had precipitated. The collected solid was washed with methyl alcohol, and the wash liquid was mixed with the filtrate from collection of the solid, and this liquid was concentrated under reduced pressure. The resulting residue was taken up in a mixture of diethyl ether and dilute ammonium hydroxide, and the aqueous layer was separated, extracted with diethyl ether, and combined with the first ether layer. This ethereal solution was washed with water, dried, and filtered. When the filtrate was mixed with ethereal hydrogen chloride solution, a solid precipitated. This product was collected on a filter, washed with diethyl ether, and dried overnight at 70°C. to yield 21.7 g. of solid. A 6 g. portion of this product was recrystallized from ethyl acetate, ethyl alcohol, and diethyl ether. Another crop of solid was recovered by working up the mother liquor and this was combined with the first crop and recrystallized from ethyl acetate. There was thus obtained 3.5 g. of 1,2,3,4,5,6-hexahydro-1-oxo-3-allyl-8-methoxy-6(eq),11(ax)-dimethyl-2,6-methano-3-benzazocine hydrochloride as a white solid which melted at 205.0°–207.6°C. (dec.)(corr.).

EXAMPLE 21

A.

To a stirred mixture of 5.0 g. of 1,2,3,4,5,6-hexahydro-1(eq),8-dihydroxy-6(eq),11(ax)-dimethyl-2,6-methano-3-benzazocine, 3.5 g. of sodium bicarbonate, and 6 ml. of N,N-dimethylformamide there was added dropwise a solution of 3.9 g. of 1-bromo-3-methyl-2-butene in 13 ml. of N,N-dimethylformamide. The mixture was stirred and refluxed for 1 hour, and then cooled and filtered, rinsing the solid thus collected with methyl alcohol. The filtrate, including the methanolic wash liquor, was concentrated under reduced pressure to yield a residual mixture of crystalline solid and oil. This residue was taken up in a mixture of dilute ammonium hydroxide and chloroform, the chloroform and aqueous layers were separated and the aqueous layer was extracted with chloroform. The chloroform solutions were combined, washed with water, dried, and filtered. The filtrate was concentrated under reduced pressure and the resulting residue was taken up in diethyl ether. The ether solution was cooled in an ice bath and the crystalline solid which separated from solution was collected on a filter and dried for 2 hours at 70°C. This solid, which weighed 3.3 g. and melted at 175°–177°C., was recrystallized from aqueous methyl alcohol and dried overnight at 70°C. There was thus obtained 2.2 g. of 1,2,3,4,5,6-hexahydro-1(eq),8-dihydroxy-3-(3-methyl-2-butenyl)-6(eq),11(ax)-dimethyl- 2,6-methano-3-benzazocine as a white solid which melted at 175.0°–176.6°C. (corr.).

B.

Using a procedure similar to that described above in part A, but using cis-1,3-dichloro-1-propene instead of 1-bromo-3-methyl-2-butene, there is obtained 1,2,3,4,5,6-hexahydro-1(eq),8-dihydroxy-3-(cis-3-chloro-2-propenyl)-6(eq),11(ax)-dimethyl-2,6-methano-3-benzazocine.

EXAMPLE 22

A mixture of 28.2 g. of 1,2,3,4,5,6-hexahydro-1-oxo-8-methoxy-6(eq),11(ax)-dimethyl-2,6-methano-3-benzazocine hydrochloride, 25.2 g. of sodium bicarbonate, and 200 ml. of N,N-dimethylformamide was stirred and there was added dropwise a solution of 18.2 g. of 1-bromo-3-methyl-2-butene in 70 ml. of N,N-dimethylformamide. The reaction mixture was then refluxed for 1 ½ hours, cooled, and filtered. The filtrate was concentrated under reduced pressure and the resulting residue was taken up in a mixture of diethyl ether and dilute ammonium hydroxide. The aqueous layer was separated and extracted with diethyl ether, and the ether extract was combined with the ether layer, washed with water, dried, treated with decolorizing charcoal, and filtered. When the filtrate was treated with ethereal hydrogen chloride solution a crystalline solid formed. The mixture was cooled in ice for one-half hour and the solid was collected on a filter, washed with diethyl ether and dried under reduced pressure for 1 hour at 60°C. There was thus obtained 33.0 g. of white crystals which melted at 219°–220°C. A 5.0 g. portion of this product was recrystallized from ethyl alcohol-diethyl ether to yield 3 g. of 1,2,3,4,5,6-hexahydro-1-oxo-3-(3-methyl-2-butenyl)-8-methoxy-6(eq),11(ax)-dimethyl-2,6-methano-3-benzazocine hydrochloride as a white crystalline solid which melted at 220.0°–220.6°C. (dec.)(corr.).

EXAMPLE 23

A mixture of 11.5 g. of 1,2,3,4,5,6-hexahydro-1-oxo-8-hydroxy-6(eq),11(ax)-dimethyl-2,6-methano-3-benzazocine, 4 ml. of 35 percent aqueous formaldehyde solution and 0.2 g. of palladium-on-charcoal hydrogenation catalyst was hydrogenated for 4 hours at 50 pounds per square inch hydrogen pressure, the mixture being warmed during the latter portion of the hydrogenation. From the hydrogenation mixture there was obtained 10.1 g. of solid which when recrystallized from ethyl alcohol yielded 5.6 g. of 1,2,3,4,5,6-hexahydro-1-oxo-3-methyl-8-hydroxy-6(eq),11(ax)-dimethyl-2,6-methano-3-benzazocine as an off-white solid which melted at 224°–228°C.

EXAMPLE 24

When 7.0 g. of 1,2,3,4,5,6-hexahydro-1-oxo-8-methoxy-6(eq),11(ax)-dimethyl-2,6-methano-3-benzazocine, 3.0 ml. of 38% formalin solution, and 3.0 ml. of formic acid were mixed together, there was immediate gas evolution from the mixture. This reaction mixture was allowed to stand at room temperature for 30 minutes with occasional swirling of the mixture within its container and was then heated on a steam bath for one hour. There were added water, diethyl ether, and ammonium hydroxide and the mixture was extracted with diethyl ether. The ether was washed with water, dried, and concentrated under reduced pressure to yield 5.2 g. of glassy residue which crystallized. This solid was dissolved in 10 ml. of ethyl alcohol, the solution was cooled, and the solid which separated from solution was collected on a filter, washed with ethyl alcohol and dried overnight at 70°C. The filtrate and wash liquor were combined and heated on a steam bath and then diluted with water until turbidity appeared. The solution was then concentrated under reduced pressure to yield a residue which crystallized. This product was dissolved in a small volume of hot ethanol and the solution was cooled and the solid which crystallized was collected on a filter, washed with n-hexane and air-dried. Using thin layer chromatography, this product was separated into two fractions, one weighing 2.9 g., m.p. 109°–113°C. and the other weighing 1.3 g., m.p. 108°–112°C. The 2.9 g. fraction was recrystallized twice from ethyl alcohol to yield 1 g. of 1,2,3,4,5,6-hexahydro-1-oxo-3,6(eq),11(ax)-trimethyl-8-methoxy-2,6-methano-3-benzazocine as a yellow solid which melted at 109°–111°C.

EXAMPLE 25

A.

To a stirred mixture of 5.0 g. of 1,2,3,4,5,6-hexahydro-1(eq),8-dihydroxy-6(eq),11(ax)-dimethyl-2,6-methano-3-benzazocine, 3.5 g. of sodium bicarbonate, and 60 ml. of N,N-dimethylformamide there was added dropwise a solution of 3.2 g. of allyl bromide in 17 ml. of N,N-dimethylformamide. The mixture was stirred and refluxed for 3 ¼ hours, filtered, and the solid thus collected was rinsed with methyl alcohol. The filtrate, including the methanolic wash liquor, was concentrated under reduced pressure. The residue thus obtained was taken up in a mixture of dilute ammonium hydroxide and chloroform. The chloroform and aqueous layers were separated and the aqueous layer was extracted with chloroform, and the chloroform extract was combined with the chloroform layer, washed with water, dried, treated with decolorizing charcoal, and filtered. The filtrate was concentrated under reduced pressure to yield 9.1 g. of a dark oil. This oil was dissolved in 10 ml. of acetone and the solution was concentrated under reduced pressure to yield 7.0 g. of oil. This oil was chromatographed on 350 g. of silica, eluting with chloroform-methanol-isopropylamine. The collected fraction of product was concentrated under reduced pressure to yield 5.2 g. of solid which was recrystallized from diethyl ether-hexane mixture and dried overnight at 70°C. There was thus obtained 2.8 g. of a solid which melted at 144°–148°C. When this product was recrystallized from hexane-acetone mixture there was obtained 1.4 g. of 1,2,3,4,5,6-hexahydro-1(eq),8-dihydroxy-3-allyl-6(eq),11(ax)-dimethyl-2,6-methano-3-benzazocine as a white solid which melted at 148°–150°C.

B.

Proceeding in a fashion similar to that described in part A, but using cyclobutylmethyl bromide, cyclohexylmethyl bromide, 2-cyclopropylethyl bromide, 4-cyclobutylbutyl bromide, (1-fluorocyclopropyl)methyl bromide, and 2,2-difluorocyclopropylmethyl bromide instead of allyl bromide there are obtained, respectively, the following N-alkylation products which, by esterification with the appropriate acid chlorides as illustrated in Examples 6–17 above, can be converted to the indicated respective esters:

1,2,3,4,5,6-hexahydro-1(eq),8-dihydroxy-3-cyclobutylmethyl-6(eq),11(ax)-dimethyl-2,6-methano-3-benzazocine and the corresponding 8-(p- acetamidobenzoyloxy) ester;

1,2,3,4,5,6-hexahydro-1-hydroxy-3-cyclohexylmethyl-8-hydroxy-6(eq),11(ax)-dimethyl-2,6-methano-3-benzazocine and the corresponding 8-phenoxyacetoxy and 1,8-bis(phenoxyacetoxy) esters;

1,2,3,4,5,6-hexahydro-1(eq),8-dihydroxy-3-(2-cyclopropylethyl)-6(eq),11(ax)-dimethyl-2,6-methano-3-benzazocine and the corresponding 8-(2-naphthalenecarbonyloxy) and 1,8-bis(2-naphthalenecarbonyloxy) esters;

1,2,3,4,5,6-hexahydro-1-hydroxy-3-(4-cyclobutylbutyl)-8-hydroxy-6(eq),11(ax)-dimethyl-2,6-methano-3-benzazocine and the corresponding 8-nicotinoyloxy and 1,8-bis(nocotinoyloxy) esters;

1,2,3,4,5,6-hexahydro-1-hydroxy-1(eq),8-dihydroxy-3-[(1-fluorocyclopropyl)methyl]-6(eq),11(ax)-dimethyl-2,6-methano-3-benzazocine and the corresponding 8-(1-fluorocyclopropanecarbonyloxy) and 1,8-bis(1-fluorocyclopropanecarbonyloxy) esters; and 1,2,3,4,5,6-hexahydro-1(eq),8-dihydroxy-3-(2,2-difluorocyclopropylmethyl)-6(eq),11(ax)-dimethyl-2,6-methano-3-benzazocine and the corresponding 8-acetoxy and 8-acetoxy-1-cyclopropanecarbonyloxy esters.

C.

Proceeding in a manner similar to that described above in part A, but using 1,2,3,4,5,6-hexahydro-1(eq),8-dihydroxy-2,6-methano-3-benzazocine instead of 1,2,3,4,5,6-hexahydro-1(eq),8-dihydroxy-6(eq),1-1(ax)-dimethyl-2,6-methano-3-benzazocine, there is obtained 1,2,3,4,5,6-hexahydro-1(eq),8-dihydroxy-3-allyl-2,6-methano-3-benzazocine.

EXAMPLE 26

A.

Proceeding in a manner similar to that described above in Example 21, 5.0 g. of 1,2,3,4,5,6-hexahydro-1-oxo-8-hydroxy-6(eq),11(ax)-dimethyl-2,6-methano-3-benzazocine was interacted with 3.9 g. of 1-bromo-3-methyl-2-butene in N,N-dimethylformamide to yield 1.7 g. of 1,2,3,4,5,6-hexahydro-1-oxo-3-(3-methyl-2-butenyl)-8-hydroxy-6(eq),11(ax)-dimethyl-2,6-methano-3-benzazocine as a white solid which melted at 174.0°–175.2°C. (corr.).

B.

Proceeding in a manner similar to that described above in part A, by interaction of 1,2,3,4,5,6-hexahydro-1-oxo-8-hydroxy-6(eq),11(ax)-dimethyl-2,6-methano-3-benzazocine with 1-bromo-2,3-dimethyl-2-butene, 1,1,2,3-tetrachloro-1-propene, 1,1,3-tribromo-1-propene, 1,2-difluoro-3-methyl-2-butene, 1-bromo-3,3-dicyano-2-propene, and propargyl bromide there are obtained, respectively, the following N-alkylation products which by esterification with the appropriate acid chloride, as illustrated in Examples 6–17 above, can be converted to the indicated respective esters:

1,2,3,4,5,6-hexahydro-1-oxo-3-(2,3-dimethyl-2-butenyl)-8-hydroxy-6(eq),11(ax)-dimethyl-2,6-methano-3-benzazocine and the corresponding 8-stearoyloxy ester;

1,2,3,4,5,6-hexahydro-1-oxo-3-(2,3,3-trichloro-2-propenyl)-8-hydroxy-6(eq),11(ax)-dimethyl-2,6-methano-3-benzazocine and the corresponding 8-(p-toluyloxy) ester;

1,2,3,4,5,6-hexahydro-1-oxo-3-(3,3-dibromo-2-propenyl)-8-hydroxy-6(eq),11(ax)-dimethyl-2,6-methano-3-benzazocine and the corresponding 8-benzoyloxy ester;

1,2,3,4,5,6-hexahydro-1-oxo-3-(2-fluoro-3-methyl-2-butenyl)-8-hydroxy-6(eq),11(ax)-dimethyl-2,6-methano-3-benzazocine and the corresponding 8-(cis-9-octadecenoyloxy) ester;

1,2,3,4,5,6-hexahydro-1-oxo-3-(3,3-dicyanoallyl)-8-hydroxy-6(eq),11(ax)-dimethyl-2,6-methano-3-benzazocine and the corresponding 8-(m-trifluorobenzoyloxy) ester; and 1,2,3,4,5,6-hexahydro-1-oxo-3-propargyl-8-hydroxy-6(eq),11(ax)-dimethyl-2,6-methano-3-benzazocine and the corresponding 8-(p-dimethylaminophenylacetoxy) ester.

EXAMPLE 27

A mixture of 5.6 g. of 1,2,3,4,5,6-hexahydro-1(eq)-hydroxy-8-methoxy-6(eq),11(ax)-dimethyl-2,6-methano-3-benzazocine hydrochloride, 3.7 g. of 2,2-dimethoxyethyl bromide, 5.1 g. of sodium bicarbonate, and 100 ml. of N,N-dimethylformamide was stirred and refluxed for 4½ hours. The reaction mixture was cooled and filtered, and the filtrate was concentrated under reduced pressure. The residue was taken up in a mixture of diethyl ether and water, the aqueous layer was separated and extracted with diethyl ether, and the ethereal solutions were combined, washed with water, dried, and concentrated to yield 5.5 g. of crude product. This product was chromatographed on 300 g. of silica gel using benzene-isopropylamine (97:1, $\gamma/\gamma$) for elution. The fraction containing the product was collected and concentrated under reduced pressure to yield 1,2,3,4,5,6-hexahydro-1(eq)-hydroxy-3-(2,2-dimethoxyethyl)-8-methoxy-6(eq),11(ax)-dimethyl-2,6-methano-3-benzazocine. This base was converted to its hydrochloride, a white solid which weighed 4.7 g. and melted at 160°–163°C. (dec.). This salt, after recrystallization from methanol-ether, weighed 2.7 g. and melted at 166°C. (dec.).

EXAMPLE 28

A mixture of 1.2 g. of 1,2,3,4,5,6-hexahydro-1(eq)-hydroxy-1-phenyl-8-methoxy-6(eq),11(ax)-dimethyl-2,6-methano-3-benzazocine and 0.8 g. of methyl trichloroacetate was heated on a steam bath for four hours and the resulting product was taken up in 6 ml. of hot ethyl alcohol. On cooling, 800 mg. of crystals, m.p. 158°–161°C., was obtained. Recrystallization of this product from 90 per cent ethyl alcohol yielded 600 mg. of 1,2,3,4,5,6-hexahydro-1(eq)-hydroxy-1-phenyl-3,6(eq),11(ax)-trimethyl-2,6-methano-3-benzazocine which melted at 161°–163°C.

EXAMPLE 29

A.

A Grignard reagent was prepared by adding a 5 ml. portion of a solution of 6.3 g. of bromobenzene in 30 ml. of anhydrous diethyl ether to 1.1 g. of magnesium turnings, heating the reaction mixture to reflux temperature on a steam bath, and then adding the remainder of the bromobenzene solution at a rate sufficient to maintain refluxing. After this addition was completed, the reaction mixture was refluxed for one-half hour. To the mixture thus obtained there was added dropwise a solution of 5.2 g. of 1,2,3,4,5,6-hexahydro-1-oxo-3,6(eq),11(ax)-trimethyl-2-methoxy-2,6-methano-3-benzazocine in 60 ml. of anhydrous diethyl ether. The reaction mixture was stirred and refluxed for 7 hours and then was poured into a mixture of water and ice. Two layers formed in the resulting mixture. The aqueous layer was separated and extracted with several small portions of diethyl ether. The ether extracts were combined, washed successively with N sodium hydroxide solution and with water, and then dried and filtered. The filtrate was concentrated under reduced pressure to yield 4.2 g. of crude 1,2,3,4,5,6-hexahydro-1(eq)-hydroxy-1-phenyl-3,6(eq),11(ax)-trimethyl-8-methoxy-2,6-methano-3-benzazocine which melted at 153°–156°C. Recrystallization of this product from ethyl alcohol yielded 3.3 g. of the purified base as a white product which melted at 161°–163°C. This product was identical with that described in Example 28 hereinabove.

B.

When the procedure in part A is carried out using p-bromoanisole instead of bromobenzene and 1,2,3,4,5,6-hexahydro-1-oxo-3-cyclopropylmethyl-8-methoxy-6(eq),11(ax)-dimethyl-2,6-methano-3-benzazocine instead of 1,2,3,4,5,6-hexahydro-1-oxo-3,6(eq),11(ax)-trimethyl-8-methoxy-2,6-methano-3-benzazocine, there is obtained 1,2,3,4,5,6-hexahydro-1(eq)-hydroxy-1(ax)-(p-methoxyphenyl)-3-cyclopropylmethyl-8-methoxy-6(eq),11(ax)-dimethyl-2,6-methano-3-benzazocine.

EXAMPLE 30

A solution of 15.26 g. of 1,2,3,4,5,6-hexahydro-1-oxo-3-cyclopropanecarbonyl-8-cyclopropanecarbonyloxy-6(eq),11(ax)-dimethyl-2,6-methano-3-benzazocine in 100 ml. of tetrahydrofuran was added dropwise to 4.5 g. of lithium aluminum hydride covered with 50 ml. of tetrahydrofuran. The reaction mixture was refluxed for 4 hours and then cooled and 9.0 ml. of water was added. The mixture was diluted to a volume of 1200 ml. with tetrahydrofuran, diatomaceous silica was added, and the mixture was boiled for 10 minutes and filtered. The residue thus collected was washed with hot tetrahydrofuran and the filtrate including the tetrahydrofuran wash liquor was concentrated under reduced pressure to yield 15.0 g. of oily residue. The residue was treated with ethereal hydrogen chloride and the solid which precipitated was collected on a filter, washed with diethyl ether, and dried at 70°C. The filtrate was concentrated under reduced pressure to yield 2.2 g. of solid which was recrystallized three times from ethyl alcohol-diethyl ether mixture and then from isopropyl alcohol-diethyl ether mixture. There was thus obtained 2.0 g. of 1,2,3,4,5,6-hexahydro-1(eq),8-dihydroxy-3-cyclopropylmethyl-6(eq),11(ax)-dimethyl-2,6-methano-3-benzazocine hydrochloride as an off-white solid which melted at 230.0°–231.0°C. (dec.)(corr.).

EXAMPLE 31

A.

A solution of 8.6 g. of 1,2,3,4,5,6-hexahydro-1-oxo-3-allyl-8-methoxy-6(eq),11(ax)-dimethyl-2,6-methano-3-benzazocine in 100 ml. of tetrahydrofuran was added dropwise to 1.1 g. of lithium aluminum hydride in 50 ml. of tetrahydrofuran. The mixture was refluxed for 2 hours and then cooled and 2.2 ml. of water was added dropwise. The reaction mixture was filtered and the filtrate was concentrated under reduced pressure. The resulting residue was taken up in a mixture of chloroform and dilute hydrochloric acid. The chloroform and aqueous layers were separated, and the aqueous layer was extracted with chloroform and the chloroform extract was added to the chloroform layer. The chloroform solution was washed with dilute ammonium hydroxide and then with water, dried, and concentrated under reduced pressure to yield 7.4 g. of light yellow oil. This oil, which was crude 1,2,3,4,5,6-hexahydro-1(eq)-hydroxy-3-allyl-8-methoxy-6(eq),11(ax)-dimethyl-2,6-methano-3-benzazocine, was chromatographed on 400 g. of silica, eluting with chloroform-methanol-isopropyl-amine mixture (94:3:3, v/v/v). The fractions having $R_f$=0.70 were combined, concentrated, and treated with ethereal hydrogen chloride solution. The precipitate which formed was collected on a filter and dried overnight under reduced pressure. The solid thus obtained, which weighed 5.1 g. and melted at 235°–238°C., was recrystallized from isopropyl alcohol-diethyl ether and dried overnight at 70°C. There was thus obtained 4.2 of 1,2,3,4,5,6-hexahydro-1(eq)-hydroxy-3-allyl-8-methoxy-6(eq),11(ax)-dimethyl-2,6-methano-3-benzazocine hydrochloride as a white solid which melted at 238.0°–239.0°C. (dec.)(corr.).

B.

When 1,2,3,4,5,6-hexahydro-1-oxo-3-(p-nitrophenethyl)-8-methoxy-6(eq),11(ax)-dimethyl-2,6-methano-3-benzazocine is used in the procedure described in part A instead of 1,2,3,4,5,6-hexahydro-1-oxo-3-allyl-8-methoxy-6(eq),11(ax)-dimethyl-2,6-methano-3-benzazocine, there is obtained 1,2,3,4,5,6-hexahydro-1(eq)-hydroxy-3-(p-aminophenethyl)-8-methoxy-6(eq),11(ax)-dimethyl-2,6-methano-3-benzazocine.

C.

When 1,2,3,4,5,6-hexahydro-1-oxo-3-(cis-3-chloro-2-propenyl)-8-methoxy-2,6-methano-3-benzazocine is used in the procedure described in part A instead of 1,2,3,4,5,6-hexahydro-1-oxo-3-allyl-8-methoxy-6(eq),11(ax)-dimethyl-2,6-methano-3-benzazocine, there is obtained 1,2,3,4,5,6-hexahydro-1(eq)-hydroxy-3-(cis-3-chloro-2-propenyl)-8-methoxy-2,6-methano-3-benzazocine.

EXAMPLE 32

To 8.75 g. of N-(carbo-t-butoxy)glycine in 100 ml. of acetone (incomplete solution) there were added at −20°C. 7.0 ml. of triethylamine and 7.0 ml. of isobutyl chloroformate. The mixture was stirred for five minutes and while continuing to maintain the temperature of the reaction mixture at −10°C. or below there was added dropwise with stirring a solution of 12.2 g. of 1,2,3,4,5,6-hexahydro-1-oxo-8-methoxy-6(eq),11(ax)-dimethyl-2,6-methano-3-benzazocine in 50 ml. of chloroform. The reaction mixture was stirred for 15 minutes and then allowed to warm to room temperature while stirring for another 6¼ hours. The reaction mixture was filtered to remove triethylamine hydrochloride, which was washed with acetone, and the filtrate including the wash liquor was concentrated under reduced pressure. The resulting residue was taken up in chloroform/water and the chloroform layer was separated, washed successively with dilute hydrochloric acid, aqueous sodium bicarbonate solution, and water, dried, and filtered. The filtrate was concentrated to yield 24.4 g. of a light-orange glass. This product was dissolved in ethyl alcohol and the solution was chilled for one week in a refrigerator. The solid which crystallized from the solution was collected on a filter and washed with ethyl alcohol. There was thus obtained 11.3 g. of 1,2,3,4,5,6-hexahydro-1-oxo-3-[N-(carbo-t-butoxy)aminoacetyl]-8-methoxy-6(eq),11(ax)-dimethyl-2,6-methano-3-benzazocine as an off-white solid which melted at 165°–170°C. Recrystallization from ethyl alcohol yielded 9.9 g. of the product which melted at 165°–168°C. (fast heating).

EXAMPLE 33

To a solution of 10.4 g. of N-(carbobenzyloxy)-glycine in 50 ml. of acetone there was added dropwise with stirring 7.0 ml. of triethylamine. The resulting mixture was cooled to −10°C. and 7.0 ml. of isobutyl chloroformate was gradually added with stirring while maintaining the temperature of the reaction mixture in the approximate range −7° to −13°C. After this addition was completed, the reaction mixture was stirred for 5 minutes at −10°C. and then there was added, in a single portion, a mixture of 14.1 g. of 1,2,3,4,5,6-hexahydro-1-oxo-8-methoxy-6(eq),11(ax)-dimethyl-2,6-methano-3-benzazocine hydrochloride, 5.1 g. of triethylamine, and 65 ml. of chloroform. The mixture thus obtained was stirred for 3¼ hours, allowing the reaction mixture to warm to room temperature, and then was filtered to remove the white precipitate which had formed. The solid thus collected was washed with three portions of acetone and the original filtrate and the wash liquors were combined and concentrated under reduced pressure. The concentrated residue was taken up in a mixture of water and diethyl ether. The ether layer was separated and the aqueous layer was extracted several times with diethyl ether. The ethereal solutions were combined and washed first with dilute hydrochloric acid, then with aqueous sodium bicarbonate solution, and finally with water and then dried over anhydrous calcium sulfate. Since the product crystallized on the drying agent, the ether was removed by evaporation, and acetone was added to dissolve the product. The acetone solution was filtered, the collected solid was washed with hot acetone, and the acetone solutions were combined and diethyl ether was added. The crystalline solid which separated was collected on a filter and dissolved in 600 ml. of hot acetone, and this solution was diluted with 1 liter of diethyl ether and chilled. The solid which separated from solution was collected on a filter, washed with diethyl ether, and dried. There was thus obtained 3.1 g. of 1,2,3,4,5,6-hexahydro-1-oxo-3-[N-(carbobenzyloxy)aminoacetyl]-8-methoxy-6(eq),11(ax)-dimethyl-2,6-methano-3-benzazocine as a white solid which melted at 173°–174°C.

EXAMPLE 34

To a 10.5 g. of 1,2,3,4,5,6-hexahydro-1(eq)-hydroxy-8-methoxy-6(eq),11(ax)-dimethyl-2,6-methano-3-benzazocine hydrochloride in 25 ml. of chloroform there was added 13 ml. of a solution of 3.0 g. of sodium hydroxide in 25 ml. of water. The resulting mixture was stirred and cooled in an ice-salt mixture, and there was added dropwise 4.0 g. of ethyl chloroformate in 10 ml. of chloroform. When half of this addition had been made, the remainder of the sodium hydroxide solution was added simultaneously with the remainder of the ethyl chloroformate in chloroform. After completion of these additions, stirring was continued for a minute or so. The organic and aqueous layers in the reaction mixture were separated, the aqueous layer was extracted with chloroform, and this extract and the organic layer were combined, dried, and filtered, and the filtrate was concentrated to yield 12.6 g. of a syrup. This syrup was taken up in boiling hexane, and the solution thus obtained was cooled. The crystalline solid which separated from solution was collected on a filter, washed with hexane, and dried at 70°C. This product, which weighed 9.7 g. and melted at 130°–131°C. was recrystallized from hexane to yield 4.7 g. of 1,2,3,4,5,6-hexahydro-1(eq)-hydroxy-3-carethoxy-8-methoxy-6(eq),11(ax)-dimethyl-2,6-methano-3-benzazocine as a white solid which melted at 131°–132°C.

EXAMPLE 35

A mixture of 9.0 g. of 1,2,3,4,5,6-hexahydro-1(eq)-hydroxy-1(ax),6(eq),11(ax)-trimethyl-8-methoxy-2,6-methano-3-benzazocine hydrochloride, 25 ml. of chloroform, and 12 ml. of a solution of 2.5 g. of sodium hydroxide in 25 ml. of water was stirred vigorously and cooled in an ice-salt water bath, and there was added dropwise a solution of 3.6 g. of ethyl chloroformate in 10 ml. of chloroform. When approximately half of the solution had been added, the remainder of the sodium hydroxide solution was added simultaneously with the remainder of the ethyl chloroformate solution. After completion of these additions, the reaction mixture was stirred for 10 minutes. The organic and aqueous layers in the reaction mixture were separated, the aqueous layer was extracted with chloroform, and this extract and the organic layer were combined, washed with water, dried, and filtered. The filtrate was concentrated to yield 10.1 g. of a syrup. This syrup was taken up in boiling hexane, and the solution thus obtained was cooled. The crystalline solid which separated from solution was collected on a filter, washed with hexane, and dried at 70°C. This product, which weighed 8.3 g. and melted at 109°–112°C., was recrystallized from hexane to yield 2.9 g. of 1,2,3,4,5,6-hexahydro-1(eq)-hydroxy-1(ax),6(eq),11(ax)-trimethyl-3-carbethoxy-8-methoxy-2,6-methano-3-benzazocine as an off-white solid which melted at 99°–101°C.

EXAMPLE 36

To a solution of 5.8 g. of 1,2,3,4,5,6-hexahydro-1(eq)-hydroxy-3-carbethoxy-8-methoxy-6(eq),11(ax)-dimethyl-2,6-methanol-3-benzazocine in toluene there was added 0.5 g. of aluminum isopropoxide. The solvent was slowly distilled off until the vapor temperature reached 110°C. The solution was then washed successively with dilute hydrochloric acid, water, aqueous sodium bicarbonate solution, and water, after which the solvent was distilled off under reduced pressure. The residue thus obtained was dissolved in hot acetone, and hot hexane was added to the solution. The solid which separated from solution or chilling was collected on a filter, washed with hexane, dried at 70°C. thus obtained 4.1 g. of 7-methoxy-3a,4,5,9b-tetrahydro-4(ax),5(eq)-dimethyl-3,5-ethanonaphth[2,1-d]oxazol-2(3H)-one as a white solid which melted at 135°–136°C.

EXAMPLE 37

Proceeding in a manner similar to that described above in Example 36, a solution of 5.0 g. of 1,2,3,4,5,6-hexahydro-1(eq)-hydroxy-1(ax),6(eq),11(ax)-trimethyl-3-carbethoxy-8-methoxy-2,6-methano-3-benzazocine in toluene to which was added 0.5 g. of aluminum isopropoxide was gradually distilled for 3 hours, until the vapor temperature reached 110°C. From the resulting reaction mixture there was obtained 2.3 g. of 3a,4,5,9b-tetrahydro-7-methoxy-4(ax),-5(eq),9b(ax)-trimethyl-3,5-ethanonaphth[2,1-d]oxazol-2(3H)-one as a white solid which melted at 137°–139°C.

EXAMPLE 38

To a solution of 4.8 g. of 1,2,3,4,5,6-hexahydro-1(eq)-hydroxy-1-phenyl-8-methoxy-6(eq),11(ax)-dimethyl-2,6-methano-3-benzazocine in 100 ml. of anhydrous ethyl alcohol there was added 3.6 g. of triethylamine. When phosgene gas was bubbled into the resulting solution, a white solid formed. The treatment with phosgene was discontinued after ½ hour, diethyl ether was added, and the mixture was filtered. The solid thus collected was washed twice with water and dried under reduced pressure at 50°C. overnight. This poduct (2.7 g.) was combined with a further crop weighing 0.9 g. recovered from the ethereal filtrate and recrystallized twice from 90 per cent ethyl alcohol. There was thus obtained 2.45 g. of 7-methoxy-4(ax),-5(eq)-dimethyl-9b(ax)-phenyl-3a,4,5,9b-tetrahydro-3,5-ethanonaphth[2,1-d]-oxazol-2(3H)-one as a white solid which softened at 170°C. and melted at 192°–194°C.

EXAMPLE 39

To a solution obtained by dissolving 20 g. of 1,2,3,4,5,6-hexahydro-6(eq),11(ax)-dimethyl-2,6-methano-3-benzazocine in cold dilute sulfuric acid (prepared by dissolving ice in 90 ml. of concentrated sulfuric acid to a final volume of 325 ml.) there was added 40 g. of chromium trioxide. The resulting reaction mixture was stirred and heated on a steam bath for 1 hour and then was poured onto ice and 250 ml. of concentrated ammonium hydroxide was added. By extracting the crude free base product into diethyl ether, purifying it by chromatographine on silica gel, and conversion of the base to the hydrochloride there was obtained 4 g. of 1,2,3,4,5,6-hexahydro-1-oxo-6(eq),11(ax)-dimethyl-2,6-methano-3-benzazocine hydrochloride as an off-white solid. After recrystallization from ethyl alcohol- diethyl ether this product weighed 3.2 g. and melted at 251°–253°C.

EXAMPLE 40

A solution of 26.8 g. of 1,2,3,4,5,6-hexahydro-8-methoxy-6(eq),11(ax)-dimethyl-2,6-methano-3-benzazocine hydrochloride in 500 ml. of 0.5M sulfuric acid was stirred at 40°–50°C., and to this solution there was added dropwise over a period of 4 hours a solution of 13.2 g. of chromium trioxide in 500 ml. of 0.5M sulfuric acid. During this addition a precipitate appeared and then dissolved in the reaction mixture. After addition of the chromium trioxide solution was completed, the reaction mixture was stirred at 40°–50°C. for 4½ hours and then allowed to stand overnight at room temperature. There was then added to the reaction mixture a solution of 15 g. of sodium bisulfite in 50 ml. of water, followed by the dropwise addition of a solution of 138 g. of potassium carbonate in 500 ml. of water. There was added 50 ml. of concentrated ammonium hydroxide and the mixture was shaken with 500 ml. of chloroform. Diatomaceous silica was added, the mixture was filtered, and the aqueous and chloroform layers in the filtrate were separated. The aqueous layer was extracted with two 500 ml. portions of chloroform and these chloroform extracts were added to the chloroform solution and the combined solution was dried and then concentrated to yield a residue which weighed 25.5 g. This residue was taken up in 300 ml. of anhydrous diethyl ether and there was added dropwise with stirring dilute ethereal hydrogen chloride solution until precipitation was completed. The mixture was stored for 2 days in a refrigerator and was then filtered to collect the precipitated solid. The product thus collected was washed with ether and dried under reduced pressure for 2 hours at 60°C. There was thus obtained 20.3 g. of solid which melted at 262°–265°C. This product, which was 1,2,3,4,5,6-hexahydro-1-oxo-8-methoxy-6(eq),11(ax)-dimethyl-2,6-methano-3-benzazocine hydrochloride, melted at 266.0°–268.0°C. (dec.) (corr.) when recrystallized from anhydrous ethanol. Treatment of this hydrochloride with concentrated ammonium hydroxide yielded the corresponding free base.

EXAMPLE 51

A mixture of 43.6 g. of 1,2,3,4,5,6-hexahydro-1-oxo-8-methoxy-6(eq),11(ax)-dimethyl-2,6-methano-3-benzazocine hydrochloride and 200 ml. of 48% hydrobromic acid was refluxed for 5 hours. The reaction mixture was concentrated under reduced pressure, isopropyl alcohol was added, the mixture was made basic by the addition of ammonium hydroxide and then further concentrated under reduced pressure and cooled. The solid which separated from solution was recrystallized from methyl alcohol and dried overnight at 70°C. There was thus obtained 29.5 g. of solid which melted at 271°–272°C. A 5 g. portion of this solid was recrystallized from N,N-dimethylformamide to yield 3 g. of 1,2,3,4,5,6-hexahydro-1-oxo-8-hydroxy-6(eq),1-1(ax)-dimethyl-2,6-methano-3-benzazocine as an off-white solid which melted at 272.0°–274.0°C. (dec.)-(corr.).

EXAMPLE 42

A.

A mixture of 76.8 g. of 1,2,3,4,5,6-hexahydro-8-hydroxy-6(eq), 11(eq)-dimethyl-2,6-methano-3-benzazocine and 225 ml. of acetic anhydride was stirred. The mixture became warm and the nor-base dissolved, and a solid reaction product separated from solution. The reaction mixture was heated on a steam bath for 1 hour and was then filtered. The solid thus collected was washed with ether and dried under reduced pressure at 70°C. over sodium hydroxide. There was thus obtained 74.1 g. of 1,2,3,4,5,6-hexahydro-8-acetoxy-3-acetyl-6(eq),11(eq)-dimethyl-2,6-methano-3-benzazocine as a crystalline solid which melted at 196°–201°C. A small additional amount of this product was recovered by concentrating the filtrate. The combined crops were mixed with a solution of 17 g. of sodium hydroxide and 350 ml. of water and the mixture was stirred and heated on a steam bath for 1 hour to saponify the ester, 100 ml. of ethyl alcohol was added and stirring and heating were continued. There was added to the mixture dropwise 50 ml. of dimethyl sulfate, and the reaction mixture was stirred for 5 hours. The mixture was extracted twice with diethyl ether and the ether extracts were combined and washed successively with 35% aqueous sodium hydroxide solution, diluted hydrochloric acid, and water. The ether solution was then dried and concentrated under reduced pressure to yield 74.9 g. of 1,2,3,4,5,6-hexahydro-3-acetyl-8-methoxy-6(eq),1-1(eq)-dimethyl-2,6-methano-3-benzazocine as a yellow syrup. A mixture of this syrup and 500 ml. of glacial acetic acid was stirred and there was added in one portion a mixture of 36 g. of chromium trioxide and 150 ml. of water. The resulting mixture, the temperature of which rose to 70°C., was stirred for 1 hour, then heated on a steam bath for 1 hour, cooled, and concentrated under reduced pressure. The resulting residue was taken up in a mixture of ether and an aqueous solution containing 10 g. of sodium bisulfite. This mixture was extracted with diethyl ether and the ether solution was dried and filtered and the filtrate was concentrated under reduced pressure to yield 67.3 g. of 1,2,3,4,5,6-hexahydro-1-oxo-3-acetyl-8-methoxy-6(eq),11(eq)-dimethyl-2,6-methano-3-benzazocine as a syrup. (See also Example 44B below).

B. A mixture of 67.3 g. of 1,2,3,4,5,6-hexahydro-1-oxo-3-acetyl-8-methoxy-6(eq),11(eq)-dimethyl-2,6-methano-3-benzazocine, 140 ml. of concentrated hydrochloric acid, and 280 ml. of water was stirred and refluxed for 4½ hours. The reaction mixture was cooled and the solid which had separated from solution was collected on a filter, washed with methyl alcohol, and dried to yield 47.7 g. of crude 1,2,3,4,5,6-hexahydro-1-oxo-8-methoxy-6(eq),11(eq)-dimethyl-2,6-methano-3-benzazocine hydrochloride. Recrystallization of 3.0 g. of this product twice from methanol yielded 1.2 g. of the pure product as a white solid which melted at 285°C. (dec.).

EXAMPLE 43

Proceeding in a manner similar to that described above in Example 41, 29.4 g. of 1,2,3,4,5,6-hexahydro-1-oxo-8-methoxy-6(eq),11(eq)-dimethyl-2,6-methano-3-benzazocine was heated with 300 ml. of 48% hydrobromic acid to yield 29.4 of 1,2,3,4,5,6-hexahydro-1-oxo-8-hydroxy-6(eq),11(eq)-dimethyl-2,6-methano-3-benzazocine hydrobromide. By dissolving 17.9 g. of the hydrobromide in hot water, adding ammonium hydroxide to the solution, and recrystallizing the resulting precipitate from a mixture of 45 ml. each of water and N,N-dimethylformamide there was obtained 9.0 g. of 1,2,3,4,5,6-hexahydro-1-oxo-8-hydroxy-6(eq),11(eq)-dimethyl-2,6-methano-3-benzazocine as an off-white solid which melted at 258°–259°C.

EXAMPLE 44

A.
A mixture of 1,2,3,4,5,6-hexahydro-1-oxo-8-methoxy-6(eq),11(ax)-dimethyl-2,6-methano-3-benzazocine and 60 ml. of acetic anhydride was allowed to stand overnight at room temperature (approximately 25°C.). The reaction mixture was evaporated to dryness under reduced pressure, the resulting residue was dissolved in 70 ml. of ethyl alcohol, and the solution was cooled. The solid which separated from solution was collected on a filter, washed with ethyl alcohol, and air-dried. This product weighed 5.8 g. and melted at 121°–123°C. A further crop of solid weighing 7.3 g. and melting at 121°–123°C. was recovered from the filtrate. The two crops were combined and recrystallized from ethyl acetate to yield 8.8 g. of 1,2,3,4,5,6-hexahydro-1-oxo-3-acetyl-8-methoxy-6(eq),11(ax)-dimethyl-2,6-methano-3-benzazocine as a white solid which melted at 122°–124°C.

B.
When the corresponding 6(eq),11(eq)-dimethyl isomer was used as the starting material, N-acetylation yielded 1,2,3,4,5,6-hexahydro-1-oxo-3-acetyl-8-methoxy-6(eq),11(eq)-dimethyl-2,6-methano-3-benzazocine as a white solid which melted at 121°–124°C.

C.
By mixing each of the products of parts A and B above with boron tribromide in ethylene chloride at 0°C. and allowing the mixture in each instance to warm to room temperature, there are obtained the corresponding 8-hydroxy compounds.

EXAMPLE 45

A.
To a mixture of 9.25 g. of 1,2,3,4,5,6-hexahydro-1-oxo-8-hydroxy-6(eq),11(ax)-dimethyl-2,6-methano-3-benzazocine and 130 ml. of pyridine there was added dropwise with stirring a solution of 8.36 g. of cyclopropanecarbonyl chloride in 17 ml. of anhydrous diethyl ether. The reaction mixture was stirred for 4 hours and then allowed to stand overnight. The mixture was then concentrated under reduced pressure and the resulting residue was taken up in a mixture of water and diethyl ether. The aqueous and ether layers were separated, and the ether layer was washed first with 100 ml. of 4.2 M hydrochloric acid and then with water, dried, and concentrated under reduced pressure. There was thus obtained 15.26 g. of 1,2,3,4,5,6-hexahydro-1-oxo-3-cyclopropanecarbonyl-8-cyclopropanecarbonyloxy-6(eq), 11(ax)-dimethyl-2,6-methano-3-benzazocine as a glassy oil. By treatment with weak base, such as sodium bicarbonate solution, this esteramide is converted to 1,2,3,4,5,6-hexahydro-1-oxo-3-cyclopropanecarbonyl-8-hydroxy-6(eq),11(ax)-dimethyl-2,6-methano-3-benzazocine.

B.
When 1,2,3,4,5,6-hexahydro-1-oxo-2.6-methano-3-benzazocine (obtained by N-demethylation of 1,2,3,4,5,6-hexahydro-1-oxo-3-methyl-2,6-methano-3-benzazocine with cyanogen bromide or with diethyl azodicarboxylate) is used in the procedure of part A instead of 1,2,3,4,5,6-hexahydro-1-oxo-8-hydroxy-6(eq),11(ax)-dimethyl-2,6-methano-3-benzazocine, there is obtained 1,2,3,4,5,6-hexahydro-1-oxo-3-cyclopropanecarbonyl-2,6-methano-3-benzazocine.

EXAMPLE 46

A.
A mixture of 27.3 g. of 1,2,3,4,5,6-hexahydro-1-oxo-8-methoxy-6(eq),11(ax)-dimethyl-2,6-methano-3-benzazocine and 800 ml. of glacial acetic acid was catalytically hydrogenated in the presence of 10% palladium-on-charcoal catalyst at room temperature. The reaction mixture was filtered and the filtrate was concentrated under reduced pressure to yield a glassy residue. This residue was taken up in acetone and the acetone solution was cooled for 1 hour in an ice bath. The solid which had separated from solution was collected on a filter, washed twice with diethyl ether and dried overnight at 70°C. There was thus obtained 19.5 g. of 1,2,3,4,5,6-hexahydro-1(eq)-hydroxy-8-methoxy-6(eq),11(ax)-dimethyl-2,6-methano-3-benzazocine acetate which melted at 180°–182°C. From the filtrate there was recovered an additional 8.0 g. of the product which melted at 174°–176°C.

A 5.0 g. sample of this acetate was dissolved in water and 1N sodium hydroxide solution was added to cause separation of the free base, 1,2,3,4,5,6-hexahydro-1(eq)-hydroxy-8-methoxy-6(eq),11(ax)-dimethyl-2,6-methano-3-benzazocine. The mixture was extracted with diethyl ether and the ether extract was dried and filtered, and the filtrate was acidified with ethanolic hydrogen chloride solution, thereby causing separation of an oil which crystallized rapidly. This solid was collected on a filter, washed with diethyl ether and dried at 70°C. This solid, which weighed 4.2 g. and melted at 216°–218°C., was recrystallized from ethyl alcohol-diethyl ether and then from ethyl alcohol-acetone and dried at 70°C. to yield 2.0 g. of 1,2,3,4,5,6-hexahydro-1(eq)-hydroxy-8-methoxy-6(eq),11(ax)-dimethyl-2,6-methano-3-benzazocine hydrochloride as a white solid which melted at 219.0°–220.8°C. (corr.).

This same hydrochloride was obtained by catalytic hydrogenation of 1,2,3,4,5,6-hexahydro-1-oxo-8-methoxy-6(eq),11(ax)-dimethyl-2,6-methano-3-benzazocine hydrochloride in ethanol in the presence of platinum oxide hydrogenation catalyst; but reduction of the hydrochloride failed when 10% palladium-on-charcoal hydrogenation catalyst was used.

B.

When 1,2,3,4,5,6-hexahydro-1-oxo-3-cyclopropylmethyl-8-hydroxy-6(eq),11(ax)-dimethyl-2,6-methano-3-benzazocine, 1,2,3,4,5,6-hexahydro-1-oxo-3-cyclobutylmethyl-8-hydroxy-6(eq),11(ax)-dimethyl-2,6-methano-3-benzazocine, and 1,2,3,4,5,6-hexahydro-1-oxo-3-benzyl-2,6-methano-3-benzazocine are catalytically hydrogenated in glacial acetic acid in the presence of palladium-on-charcoal hydrogenation catalyst by the procedure in part A, there are obtained, respectively:

1,2,3,4,5,6-hexahydro-1(eq),8-hydroxy-3-isobutyl-6(eq),11(ax)-dimethyl-2,6-methano-3-benzazocine;

1,2,3,4,5,6-hexahydro-1(eq),8-dihydroxy-3-cyclobutylmethyl-6(eq),11(ax)-dimethyl-2,6-methano-3-benzazocine; and 1,2,3,4,5,6-hexahydro-1-hydroxy-2,6-methano-3-benzazocine.

EXAMPLE 47

A.

A Grignard reagent was prepared by adding a solution of 28.4 g. of methyl iodide in 300 ml. of anhydrous diethyl ether dropwise to 5.7 g. of magnesium turnings covered with 100 ml. of anhydrous diethyl ether, while stirring and refluxing the mixture. After this addition was completed, the reaction mixture was refluxed for 1 hour and then was allowed to settle, and the supernatant liquid was decanted from the solid residue. This liquid was added slowly to 14.1 g. of 1,2,3,4,5,6-hexahydro-1-oxo-8-methoxy-6(eq),11(ax)-dimethyl-2,6-methano-3-benzazocine hydrochloride under 200 ml. of diethyl ether. The mixture was stirred and refluxed for 3½ hours and then was treated with aqueous ammonium chloride solution. The mixture was made basic by addition of ammonium hydroxide solution and the aqueous layer was extracted with two small portions of diethyl ether. The ether extracts were combined, dried, and filtered. The filtrate was concentrated to yield 12.1 g. of a glassy residue. This product was chromatographed on 600 g. of silica gel and eluted with chloroform-methanol-isopropylamine (94:3:3 γ/γ/γ) to yield 1,2,3,4,5,6-hexahydro-1(eq)-hydroxy-1(ax),6(eq),1-1(ax)-trimethyl-8-methoxy-2,6-methano-3-benzazocine which was treated with ethereal hydrogen chloride solution to produce 10.0 g. of the base hydrochloride as a white solid, m.p. 227°–228°C. (dec.). A sample of this salt recrystallized from ethanol-diethyl ether melted at 230°–231°C. (dec.).

B.

In the procedure described in part A, when amyl iodide is used instead of methyl iodide and 1,2,3,4,5,6-hexahydro-1-oxo-3-cyclopropylmethyl-6(eq),11(ax)-dimethyl-2,6-methano-3-benzazocine is used instead of 1,2,3,4,5,6-hexahydro-1-oxo-8-methoxy-6(eq),11(ax)-dimethyl-2,6-methano-3-benzazocine, there is obtained 1,2,3,4,5,6-hexahydro-1(eq)-hydroxy-1(ax)-amyl-3-cyclopropylmethyl-6(eq),11(ax)-dimethyl-2,6-methano-3-benzazocine.

C.

In the procedure described in part A, when 3,5-dimethylbenzyl iodide is used instead of methyl iodide and 1,2,3,4,5,6-hexahydro-1-oxo-3-cyclopropylmethyl-6(eq),11(ax)-dimethyl-2,6-methano-3-benzazocine is used instead of 1,2,3,4,5,6-hexahydro-1-oxo-8-methoxy-6(eq),11(ax)-dimethyl-2,6-methano-3-benzazocine, there is obtained 1,2,3,4,5,6-hexahydro-1(eq)-hydroxy-1(ax)-(3,5-dimethylbenzyl)-3-cyclopropylmethyl-6(eq),11(ax)-dimethyl-2,6-methano-3-benzazocine.

EXAMPLE 48

Proceeding in a manner similar to that described above in part A of Example 29, the Grignard reagent from 31.4 g. of bromobenzene and 5.7 g. of magnesium turnings was reacted with 12.2 g. of 1,2,3,4,5,6-hexahydro-1-oxo-8-methoxy-6(eq),11(ax)-dimethyl-2,6-methano-3-benzazocine in 150 ml. of anhydrous diethyl ether to yield 14.1 g. of crude 1,2,3,4,5,6-hexahydro-1(eq)-hydroxy-1-phenyl-8-methoxy-6(eq),11(ax)-dimethyl-2,6-methano-3-benzazocine. When this product was taken up in hexane, and the mixture was boiled, 10.5 g. of the purified base crystallized from the boiling mixture as a white solid which melted at 132°–135°C. After a second recrystallization from hexane, this compound melted at 132°–134°C.

EXAMPLE 49

Following a procedure similar to that described above in Example 40, 56.5 g. of 1,2,3,4,5,6-hexahydro-8-methoxy-6(eq)-ethyl-11(ax)-methyl-2,6-methano-3-benzazocine hydrochloride was oxidized by treatment with 26.4 g. of chromic oxide in dilute sulfuric acid to yield 42.3 g. of 1,2,3,4,5,6-hexahydro-1-oxo-8-methoxy-6(eq)-ethyl-11(ax)-methyl-2,6-methano-3-benzazocine, a white solid which melted at 273°–274°C. By refluxing this product with 450 ml. of 48% hydrochloric acid in a manner similar to that described above in Example 41, there was obtained 37.4 g. of 1,2,3,4,5,6-hexahydro-1-oxo-8-hydroxy-6(eq)-ethyl-11(ax)-methyl-2,6-methano-3-benzazocine, m.p. 276°–279°C. which was recrystallized from N,N-dimethylformamide to yield 29.7 g. of the product, m.p. 279°–280°C.; and a 10 g. portion of the latter was recrystallized again to yield 9.4 g. of the pure compound as a pale pink solid, m.p. 282°–284°C.

The (−)–cis isomer, prepared by similar oxidation and hydrolysis of (−)cis 1,2,3,4,5,6-hexahydro-8-methoxy-6(eq)-ethyl-11(ax)-methyl-2,6-methano-3-benzazocine hydrochloride, was obtained in the form of pale gray crystals, m.p. 275°–278°C. $[\alpha]_D^{25} = -36.2°$ (2% glacial acetic acid).

EXAMPLE 50

A.

Into a stirred solution of 3.2 g. of 1,2,3,4,5,6-hexahydro-3-cyclopropylmethyl-8-methoxy-6(eq),11(ax)-dimethyl-2,6-methano-3-benzazocine in dilute sulfuric acid (prepared by diluting 5 ml. of concentrated sulfuric acid to a volume of 50 ml. with water) there was dripped rapidly at room temperature a solution of 1.3 g. chromium trioxide in 50 ml. of dilute sulfuric acid (prepared in the same manner as before). The resulting reaction mixture was stirred for two hours on a steam bath, and then cooled and 30 ml. of concentrated ammonium hydroxide was added. The mixture was extracted with diethyl ether and the ether extract was dried and concentrated to yield 2.6 g. of crude 1,2,3,4,5,6-hexahydro-1-oxo-3-cyclopropylmethyl-8-methoxy-6(eq),11(ax)-dimethyl-2,6-methano-3-benzazocine as an oil. A 1.4 g. portion of this base was dissolved in diethyl ether and ethanolic hydrogen chloride was added to yield 1.5 g. of 1,2,3,4,5,6-hexahydro-1-oxo-3-cyclo-propylmethyl-8-methoxy-6(eq),11(ax)-dimethyl-2,6-methano-3-benzazocine hydrochloride as a white solid which melted at 193°–196°C. (dec.). When a sample of this product was mixed with a sample of the product obtained as described above in Example 14 there was no depression of the melting point.

B.

A solution of 0.7 g. of 1,2,3,4,5,6-hexahydro-1-oxo-3-cyclopropylmethyl-8-methoxy-6(eq),11(ax)-dimethyl-2,6-methano-3-benzazocine hydrochloride was cooled in an acetone-solid carbon dioxide bath and a solution of 0.52 g. of boron tribromide in 1 ml. of methylene dichloride was added. The resulting reaction mixture was allowed to warm gradually to room temperature and stand for 5 days. Then the solvent was removed by evaporation, 5 ml. of ice water was added to the residue, and the solid was collected by filtration and dried. This product (0.6 g.; m.p. 187°–193°C.) was recrystallized from water to yield 0.5 g. of 1,2,3,4,5,6-hexahydro-1-oxo-3-cyclopropylmethyl-8-hydroxy-6(eq),11(ax)-dimethyl-2,6-methano-3-benzazocine hydrochloride as a white solid which melted at 194°–200°C. This salt was treated with ammonium hydroxide to yield 0.3 g. of 1,2,3,4,5,6-hexahydro-1-oxo-3-cyclopropylmethyl-8-hydroxy-6(eq),11(ax)-dimethyl-2,6-methano-3-benzazocine as a white solid which melted at 243°–247°C. When a sample of this product was mixed with a sample of the same base prepared as described above in part A of Example 1, there was no depression of the melting point, and the two samples had identical infrared spectra.

EXAMPLE 51

A.

Following a procedure similar to that described above in Example 40, 27.1 g. of 2R,6R, 11R-1,2,3,4,5,6-hexahydro-8-methoxy-6(eq),11(ax)-dimethyl-2,6-methano-3-benzazocine hydrochloride, $[\alpha]_D^{25}$ −41.5° (1% in ethanol), (obtained by resolution of the racemic base with d(+)—tartaric acid and converting the levo-rotary tartrate via the corresponding base to the base hydrochloride) in 500 ml. of dilute sulfuric acid was oxidized by treatment with a solution of 13.4 g. of chromium trioxide in 500 ml. of dilute sulfuric acid to yield 20.5 g. of 2S,6R, 11R-1,2,3,4,5,6-hexahydro-1-oxo-8-methoxy-6(eq),11(ax)-dimethyl-2,6-methano-3-benzazocine. A 1.5 g. portion of this product was converted to the hydrochloride, which was a white solid, m.p. 254°–257°C.; $[a]_D^{25}$+ 8.4° (1% in ethanol).

B.

A mixture of 19.0 g. of 2S,6R,11R-1,2,3,4,5,6-hexahydro-1-oxo-8-methoxy-6(eq),11(ax)-dimethyl-2,6-methano-3-benzazocine and 100 ml. of 48% hydrobromic acid was refluxed for 5 hours and allowed to stand at room temperature overnight. From this reaction mixture, after making it basic by addition of ammonium hydroxide, there was isolated 4.9 g. of 2S,6R,11R-1,2,3,4,5,6-hexahydro-1-oxo-8-hydroxy-6(eq),11(ax)-dimethyl-2,6-methano-3-benzazocine, a white solid which melted at 261°–270°C. A small portion of this product was recrystallized from methyl alcohol as a white solid, m.p. 268°–269°C, $[\alpha]_D^{25}$ +95.8° (1% in ethyl alcohol).

C.

Following a procedure similar to that described above in part A of Example 1, 414 g. of 2S,6R,11R-1,2,3,4,5,6-hexahydro-1-oxo-8-hydroxy-6(eq),11(ax)-dimethyl-2,6-methano-3-benzazocine was interacted with 2.5 g. of cyclopropylmethyl bromide in the presence of 1.6 g. of sodium bicarbonate in 40 ml. of N,N-dimethylformamide to yield 2.3 g. of 2S,6R,11R-1,2,3,4,5,6-hexahydro-1-oxo-3-cyclopropylmethyl-8-hydroxy-6(eq),11(ax)-dimethyl-2,6-methano-3-benzazocine as an off-white solid, m.p. 187°–189°C., $[\alpha]_D^{25}$ −3.7° (1% in ethyl alcohol).

EXAMPLE 52

Proceeding in a manner similar to that described above in part A of Example 1, 18.7 g. of 1,2,3,4,5,6-hexahydro-1-oxo-8-hydroxy-6(eq),11(eq)-dimethyl-2,6-methano-3-benzazocine hydrobromide was interacted with 8.1 g. of cyclopropylmethyl bromide in the presence of 10.1 g. of sodium bicarbonate in 150 ml. of N,N-dimethylformamide to yield 17 g. of crude 1,2,3,4,5,6-hexahydro-1-oxo-3-cyclopropylmethyl-8-hydroxy-6(eq),11(eq)-dimethyl-2,6-methano-3-benzazocine. This base was converted to its hydrochloride and purified by repeated recrystallization from ethyl alcohol. There was thus obtained 5.4 g. of 1,2,3,4,5,6-hexahydro-1-oxo-3-cyclopropylmethyl-8-hydroxy-6(eq),11(eq)-dimethyl-2,6-methano-3-benzazocine hydrochloride hemiethanolate, $(C_{18}H_{23}NO_2.HCl)_2 \cdot C_2H_5OH$, as a white solid which melted at 257°–269°C. (dec.).

EXAMPLE 53

A.

Following a procedure similar to that described above in Example 40, 73.6 g. of 1,2,3,4,5,6-hexahydro-8-methoxy-6(eq)-ethyl-2,6-methano-3-benzazocine hydrochloride in 1 liter of dilute sulfuric acid was oxidized by treatment with a solution of 38.0 g. of chromium trioxide in 1 liter of dilute sulfuric acid, the reaction mixture thus obtained was made basic by addition of ammonium hydroxide, and then there was isolated from the reaction mixture 52.6 g. of crude 1,2,3,4,5,6-hexahydro-1-oxo-8-methoxy-6(eq)-ethyl-2,6-methano-3-benzazocine. This product was converted to the hydrochloride which was purified to yield 46.8 g. of 1,2,3,4,5,6-hexahydro-1-oxo-8-methoxy-6(eq)-ethyl-2,6-methano-3-benzazocine hydrochloride, m.p. 246°–248°C.

B.

By hydrolysis with 460 ml. of 48% hydrobromic acid and basifying the hydrolysis product with ammonium hydroxide, 45.8 g. of 1,2,3,4,5,6-hexahydro-1-oxo-8-methoxy-6(eq)-ethyl-2,6-methano-3-benzazocine hydrochloride was converted to 26.3 g. of 1,2,3,4,5,6-hexahydro-1-oxo-8-hydroxy-6(eq)-ethyl-2,6-methano-3-benzazocine as an off-white solid, m.p. 282°–284°C.

C.

Proceeding in a manner similar to that described above in part A of Example 1, 23.1 g. of 1,2,3,4,5,6-hexahydro-1-oxo-8-hydroxy-6(eq)-ethyl-2,6-methano-3-benzazocine was interacted with 13.0 g. of cyclopropylmethyl bromide in the presence of 8.4 g. of sodium bicarbonate in 230 ml. of N,N-dimethylformamide. After the reaction product was treated with ethereal hydrogen chloride, there was obtained 12.8 g. of 1,2,3,4,5,6-hexahydro-1-oxo-3-cyclopropylmethyl-8-hydroxy-6(eq)-ethyl-2,6-methano-3-benzazocine hydrochloride as an off-white solid which melted at 223°–226°C.

EXAMPLE 54

Proceeding in a manner similar to that described above in part A of Example 1, 14.7 g. of 1,2,3,4,5,6-hexahydro-1-oxo-8-hydroxy-6(eq)-ethyl-11(ax)-methyl-2,6-methano-3-benzazocine was interacted with 6.5 g. of cyclopropylmethyl bromide in the presence of 5.1 g. of sodium bicarbonate in 150 ml. of N,N-dimethylformamide to yield 3.7 g. of 1,2,3,4,5,6-hexahydro-1-oxo-3-cyclopropylmethyl-8-hydroxy-6(eq)-ethyl-11(ax)-methyl-2,6-methano-3-benzazocine as a white solid, m.p. 197°–199°C. The methanesulfonate salt of this base was a white solid, m.p. 208°–210°C. The (−)−cis isomer of the base, prepared by similar alkylation of the (−)cis nor base was obtained as off-white crystals, m.p. 196°–198°C., $[\alpha]_D^{25} = -86.4°$ (2% in glacial acetic acid).

EXAMPLE 55

A.

Following a procedure similar to that described above in Example 40, 48.4 g. of 1,2,3,4,5,6-hexahydro-8-methoxy-6(eq)-ethyl-11(eq)-methyl-2,6-methano-3-benzazocine methanesulfonate in 750 ml. of dilute sulfuric acid was oxidized by treatment with a solution of 19.8 g. of chromium trioxide in 750 ml. of dilute sulfuric acid. From the reaction mixture, after making it basic by addition of ammonium hydroxide, there was isolated 28.1 g. of crude 1,2,3,4,5,6-hexahydro-1-oxo-8-methoxy-6(eq)-ethyl-11(eq)-methyl-2,6-methano-3-benzazocine. This product was converted to the hydrochloride, a crystalline sold which after purification weighed 21.9 g.

The (+)−cis isomer of this hydrochloride, prepared by similar oxidation of the (+)-cis-1,2,3,4,5,6-hexahydro-8-methoxy-6(eq)-ethyl-11(ax)-methyl-2,6-methano-3-benzazocine hydrochloride gave the (+)cis ketone in the form of white crystals, m.p. 232°–235°C. (dec.), $[\alpha]_D^{25} = +59.8°$ (2% in methanol).

B.

By hydrolysis with 220 g. of 48% hydrobromic acid and basifying the hydrolysis product with ammonium hydroxide, 21.9 g. of 1,2,3,4,5,6-hexahydro-1-oxo-8-methoxy-6(eq)-ethyl-11(eq)-methyl-2,6-methano-3-benzazocine hydrochloride was converted to 5.5 g. of 1,2,3,4,5,6-hexahydro-1-oxo-8-hydroxy-6(eq)-ethyl-11(eq)-methyl-2,6-methano-3-benzazocine, a tan solid which melted at 264°–266°C.

C.

Proceeding in a manner similar to that described above in part A of Example 1, 10.0 g. of 1,2,3,4,5,6-hexahydro-1-oxo-8-hydroxy-6(eq)-ethyl-11(eq)-methyl-2,6-methano-3-benzazocine was interacted with 5.4 g. of cyclopropylmethyl bromide in the presence of 3.5 g. of sodium bicarbonate in 100 ml. of N,N-dimethylformamide. After the reaction mixture was acidified by treatment with ethereal hydrogey chloride, there was isolated, 1.4 g. of 1,2,3,4,5,6-hexahydro-1-oxo-3-cyclopropylmethyl-8-hydroxy-6(eq)-ethyl-11(eq)-methyl-2,6-methano-3-benzazocine hydrochloride as a light orange solid which melted at 258°–260°C.

EXAMPLE 56

A.

Proceeding in a manner similar to that described above in Example 40, 44.4 g. of 1,2,3,4,5,6-hexahydro-8-methoxy-6(eq),11(ax)-diethyl-2,6-methano-3-benzazocine in 600 ml. of dilute sulfuric acid was oxidized by treatment with a solution of 16.0 g. of chromium trioxide in 600 ml. of dilute sulfuric acid. From the reaction mixture, after making it basic by addition of ammonium hydroxide, there was isolated 32.6 g. of crude 1,2,3,4,5,6-hexahydro-1-oxo-8-methoxy-6(eq),11(ax)-diethyl-2,6-methano-3-benzazocine. A small sample of this product was recrystallized from ethyl alcohol to yield a white solid, m.p. 159°–162°C.

B.

After refluxing 17.1 g. of 1,2,3,4,5,6-hexahydro-1-oxo-8-methoxy-6(eq),11(ax)-diethyl-2,6-methano-3-benzazocine hydrochloride with 200 ml. of 48% hydrobromic acid and basifying the resulting mixture with ammonium hydroxide there was obtained 12.7 g. of 1,2,3,4,5,6-hexahydro-1-oxo-8-hydroxy-6(eq),11(ax)-diethyl-2,6-methano-3-benzazocine as a pale pink solid which melted at 247°–251°C.

C.

Using a procedure similar to that described above in part A of Example 1, 8.0 g. of 1,2,3,4,5,6-hexahydro-1-oxo-8-hydroxy-6(eq), 11(ax)-diethyl-2,6-methano-3-benzazocine was interacted with 4.1 g. of cyclopropylmethyl bromide in the presence of 2.6 g. of sodium bicarbonate in 80 ml. of N,N-dimethylformamide to yield 4.7 g. of 1,2,3,4,5,6-hexahydro-1-oxo-3-cyclopropylmethyl-8-hydroxy-6(eq),11(ax)-diethyl-2,6-methano-3-benzazocine as a tan solid which melted at 208°–212°C. By esterification of this product with p-toluyl chloride, using a procedure similar to that described above in Example 12, there is obtained 1,2,3,4,5,6-hexahydro-1-oxo-3-cyclopropylmethyl-8-(p-toluyloxy)-6(eq),11(ax)-diethyl-2,6-methano-3-benzazocine.

The following are further illustrations of the products which are obtained using the above-described procedures in accordance with this invention;

1,2,3,4,5,6-hexahydro-1-oxo-3-(cyanomethyl)-8-hydroxy-6(eq),11(ax)-dimethyl-2,6-methano-3-benzazocine and the corresponding 8-(p-anisoyloxy) ester;

1,2,3,4,5,6-hexahydro-1-oxo-3-(5-cyanoamyl)-8-hydroxy-6(eq),11(ax)-dimethyl-2,6-methano-3-benzazocine and the corresponding 8-(p-butoxyphenylacetoxy) ester;

1,2,3,4,5,6-hexahydro-1-oxo-3-(-3-cyanoallyl)-8-hydroxy-6(eq),11(ax)-dimethyl-2,6-methano-3-benzazocine and the corresponding 8-(m-fluorobenzoyloxy) ester;

1,2,3,4,5,6-hexahydro-1-oxo-3-(2,2-difluorocyclopropylmethyl)-8-hydroxy-6(eq),11(ax)-dimethyl-2,6-methano-3-benzazocine and the corresponding 8-cyclopropanecarbonyloxy ester;

1,2,3,4,5,6-hexahydro-1-oxo-3-[3-(1,3-difluorocyclohexyl)propyl]-8-hydroxy-6(eq),11(ax)-dimethyl-2,6-methano-3-benzazocine and the corresponding ethylcarbonato ester;

1,2,3,4,5,6-hexahydro-1-oxo-3-cyclobutylmethyl-8-hydroxy-6(eq),11(ax)-dimethyl-2,6-methano-3-benzazocine and the corresponding 8-(m-propionamidobenzoyloxy) ester;

1,2,3,4,5,6-hexahydro-1-oxo-3-cyclohexylmethyl-8-hydroxy-6(eq),11(ax)-dimethyl-2,6-methano-3-benzazocine and the corresponding 8-phenoxyacetoxy ester;

1,2,3,4,5,6-hexahydro-1-oxo-3-(2-cyclopropylethyl)-8-hydroxy-6-(eq),11(ax)-dimethyl-2,6-methano-3-benzazocine and the corresponding 8-(2-naphthalenecarbonyloxy) ester;

1,2,3,4,5,6-hexahydro-1-oxo-3-(4-cyclobutylbutyl)-8-hydroxy-6(eq),11(ax)-dimethyl-2,6-methano-3-benzazocine and the corresponding 8-isonicotinoyloxy ester;

1,2,3,4,5,6-hexahydro-1-oxo-3-[(1-fluorocyclopropyl)methyl]-8-hydroxy-6(eq),11(ax)-dimethyl-2,6-methano-3-benzazocine and the corresponding 8-(1-fluorocyclopropanecarbonyloxy) ester;

1,2,3,4,5,6-hexahydro-1(eq),8-dihydroxy-3-(2-cyanoethyl)-6(eq)-ethyl-11(ax)-methyl-2,6-methano-3-benzazocine;

1,2,3,4,5,6-hexahydro-1(eq),8-dihydroxy-3-(3-cyanoallyl)-6(eq)-methyl-11(ax)-ethyl-2,6-methano-3-benzazocine;

1,2,3,4,5,6-hexahydro-1(eq),8-dihydroxy-1-phenyl-3-propargyl-6(eq),11(ax)-diethyl-2,6-methano-3-benzazocine;

1,2,3,4,5,6-hexahydro-1(eq)-8-dihydroxy-3-(2-cyclohexenyl)-6(eq),11(ax)-dimethyl-2,6-methano-3-benzazocine;

1,2,3,4,5,6-hexahydro-1-oxo-3-(2-cyclopentenyl)-2,6-methano-3-benzazocine;

1,2,3,4,5,6-hexahydro-1-hydroxy-3-(2-cyclohexenylmethyl)-6(eq),11(ax)-dimethyl-2,6-methano-3-benzazocine;

1,2,3,4,5,6-hexahydro-1-oxo-3-(p-aminophenethyl)-8-hydroxy-6(eq),11(ax)-dimethyl-3-benzazocine;

1,2,3,4,5,6-hexahydro-1(eq),8-dihydroxy-3-(p-aminophenethyl)-6(eq),11(ax)-dimethyl-3-benzazocine;

1,2,3,4,5,6-hexahydro-1-oxo-3-cyclopropylmethyl-8-difluoromethoxy-6(eq),11(ax)-dimethyl-2,6-methano-3-benzazocine;

1,2,3,4,5,6-hexahydro-1-oxo-3-cyclobutylmethyl-8-trifluoromethoxy-6(eq),11(ax)-dimethyl-2,6-methano-3-benzazocine;

1,2,3,4,5,6-hexahydro-1-oxo-3-(cis-3-chloro-2-propenyl)-8-benzyloxy-6(eq),11(ax)-dimethyl-2,6-methano-3-benzazocine;

1,2,3,4,5,6-hexahydro-1-oxo-3-(2-cyclopentenyl)-8-allyloxy-6(eq),11(ax)-dimethyl-2,6-methano-3-benzazocine;

1,2,3,4,5,6-hexahydro-1-oxo-3,6(eq),11(ax)-trimethyl-8-hydroxy-2,6-methano-3-benzazocine;

1,2,3,4,5,6-hexahydro-1-oxo-3,6(eq),11(ax)-trimethyl-8-acetoxy-2,6-methano-3-benzazocine;

1,2,3,4,5,6-hexahydro-1-oxo-3-methyl-8-trifluoromethoxy-2,6-methano-3-benzazocine;

1,2,3,4,5,6-hexahydro-1-oxo-3-methyl-8-benzyloxy-6(eq)-ethyl-11(ax)-methyl-2,6-methano-3-benzazocine;

3a,4,5,9b-tetrahydro-7-trifluoromethoxy-9b-benzyl-4(ax),5(eq)-dimethyl-3,5-ethanonaphth[2,1-d]oxazol-2(3H)-one;

3a,4,5,9b-tetrahydro-9b-propyl-3,5-ethanonaphth[2,1-d]-oxazol-2(3H)-one;

1,2,3,4,5,6-hexahydro-1-oxo-8-cyclopropanecarbonyloxy-2,6-methano-3-benzazocine;

1,2,3,4,5,6-hexahydro-1-oxo-6(eq),11(ax)-dimethyl-2,6-methano-3-benzazocine;

1,2,3,4,5,6-hexahydro-1-oxo-8-trifluoromethoxy-6(eq)-ethyl-11(ax)-methyl-2,6-methano-3-benzazocine;

1,2,3,4,5,6-hexahydro-1-oxo-8-benzyloxy-6(eq),11(ax)-dimethyl-2,6-methano-3-benzazocine;

1,2,3,4,5,6-hexahydro-1-oxo-8-allyloxy-6(eq)-propyl-11(ax)-methyl-2,6-methano-3-benzazocine;

1,2,3,4,5,6-hexahydro-1-oxo-8-difluoromethoxy-6(eq),11(ax)-diethyl-2,6-methano-3-benzazocine;

1,2,3,4,5,6-hexahydro-1-oxo-3-(3-chloro-2-propenoyl)-8-hydroxy-6(eq),11(eq),11(ax)-dimethyl-2,6-methano-3-benzazocine;

1,2,3,4,5,6-hexahydro-1-oxo-3-(p-nitrophenylacetyl)-8-allyloxy-6(eq),11(ax)-dimethyl-2,6-methano-3-benzazocine;

1,2,3,4,5,6-hexahydro-1-oxo-3-cyclobutanecarbonyl-8-trifluoromethoxy-6(eq),11(ax)-diethyl-2,6-methano-3-benzazocine;

1,2,3,4,5,6-hexahydro-1-hydroxy-1-ethyl-3-(2-cyclohexenecarbonyl)-8-methoxy-2,6-methano-3-benzazocine; and 1,2,3,4,5,6-hexahydro-1-hydroxy-1-(p-methoxyphenyl)-3-caproyl-8-benzyloxy-2,6-methano-3-benzazocine.

The useful properties of the compounds of this invention were demonstrated by standard pharmacological procedures readily carried out by technicians having ordinary skill in pharmacological test procedures, so that the actual determination of the numerical biological data definitive for a particular test compound can be ascertained without the need for any extensive experimentation. Thus, in the two following test procedures the compounds of Formula I, and the species of Formula II wherein $Z^1$ is methoxy, and the species of Formula VI wherein $Z^2$ is hydroxy, acyloxy, or methoxy were found to be analgesic antagonists and analgesics.

A. Analgesic Antagonist Test

When tested in rats by a modified D'Amour-Smith thermal stimulus test procedure, the said compounds were found to be antagonists of the analgesic activity of meperidine and phenazocine. In this test procedure, when the test compounds were administered prior to or simultaneously with administration of meperidine or phenazocine, the expected analgesic effect of the latter was decreased with increasing dosage levels of the former to a point where no analgesic effect was obtained. And when the new compounds were administered after the administration off phenazocine or meperidine, the analgesic effect was diminished or terminated, depending on the dosage levels involved. For example, representative compounds of this invention, each in the form of an aqueous solution of the lactic acid-addition salt, were administered subcutaneously to rats to determine the dosage level, in terms of weight of antagonist per kilogram of body weight of the animal, which caused reduction of the analgesic effect of a 60 mg./kg. dose of meperidine hydrochloride or 0.5 mg./kg. dose of phenazocine hydrobromide by approximately 50 per cent, so that the analgesic effect produced by the combination of the antagonist and the meperidine hydrochloride, or the phenazocine hydrobromide was substantially the same as the analgesic effect produced by a 30 mg./kg. dose of meperidine hydrochloride alone or 0.25 mg./kg. of phenazocine hydrobromide alone, respectively. Test results thus obtained were in the range 1–50 mg./kg. versus meperidine and 1–75 mg./kg. versus phenazocine hydrobromide.

B. Analgesic Test - Inhibition of Acetylcholine-Induced Abdominal Constriction Response in Mice The test procedure employed was the method of H. O. J. Collier, L. C. Dineen, C. A. Johnson, and C. Schneider, British Journal of Pharmacology and Chemotherapy, 32, 295–310 (1968). The median effective doses (ED 50) (at which 50% of the mice were protected by the test compound from the abdominal constriction response) and their 95% confidence limits were calculated by probit analysis (method of Bliss). The reference drug was morphine sulfate, subcutaneously, which had ED 50 0.47 mg./kg. (confidence limits 0.38–0.56). The ED 50 values obtained with the compounds of this invention fell in the range 0.05–15 mg./kg.

A preferred aspect of this invention is the first composition aspect represented by the compounds of Formula I and their acid-addition salts, especially the pharmaceutically acceptable acid-addition salts.

Particularly preferred species of this group are 1,2,3,4,5,6-hexahydro-1-oxo-3-cyclopropylmethyl-8-hydroxy-6(eg),11(ax)-dimethyl-2,6-methano-3-benzazocine, its acid-addition salts, and the 8-acyloxy esters corresponding thereto, as illustrated in Example 6–18 inclusive. Typical test data for illustrative members of this group obtained in the above-indicated analgesic antagonist and analgesic tests were as follows:

| Analgesic Antagonism versus Phenazocine | |
|---|---|
| Compound of Example No. | AD 50 (mg. base/kg.)s.c. |
| 1A | 4.3 (2.6–7.1) |
| 1A | 5.0 (3.1–8.0) |
| 2 | 3.0 (1.9–4.8) |
| 3 | 6.0 (4.1–8.7) |
| 4 | 6.2 (3.6–10.5) |
| 5 | 38 (21–68) |
| 6 | 7.0 (4.0–12) |
| 7 | 5.2 (2.9–9.4) |

For the species of Example 1A, AD 50 values versus meperidine were: 21 (13–34) i.p. for the hydrochloride, 2.0 (1.1–3.6) s.c. for the methanesulfonate; and versus morphine were 4.0 (2.6–6.1) s.c. for the base and 4.9 (3.5–6.9) for the methanesulfonate.

| Analgesic Activity in Acetylcholine Test | | |
|---|---|---|
| Compound of Example No. | | ED 50 (mg. base/kg.) s.c. |
| 1A | (Hydrochloride) | 0.16 (0.12–0.21) |
| 1A | (Base) | 0.12 (0.09–0.15) |
| 1A | (Methanesulfonate) | 0.16 (0.14–0.19) |
| 2 | | 0.14 (0.11–0.17) |

The acute toxicity ($LD_{50}$) of the species of Example 1A in mice was as follows:

| Route | $LD_{50}$(mg/kg base ± s.e.) |
|---|---|
| i.v. | 63±2.5 |
| p.o. | 374±35 |

I claim:

1. 1,2,3,4,5,6-Hexahydro-1-($Y^1$)-1-($Y^2$)-3-($Q^2$-CO-)-8-($Z^2$)-6-($R^1$)-11-($R^2$)-2,6-methano-3-benzazocine having the formula

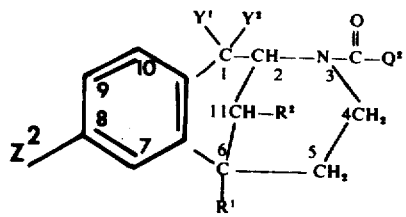

wherein:

$Y^1$ is hydroxy or acyloxy of the group consisting of: alkanoyloxy having 1–22 carbon atoms; alkenoyloxy having one or two double bonds and having 4–22 carbon atoms; Ar—$C_mH_{2m}$—CO—O— wherein $m$ is an integer from zero to two and Ar is phenyl or is phenyl substituted by 1–3 members of the group consisting of alkyl having 1–4 carbon atoms, alkoxy having 1–4 carbon atoms, halo, trifluoromethyl, dialkylamino having 2–8 carbon atoms, and alkanoylamino having 1–6 carbon atoms; phenoxyacetoxy; naphthalenecarbonyloxy; pyridinecarbonyloxy; (cycloalkyl or fluorocycloalkyl)—$C_mH_{2m}$—Co—O— having a total of 4–10 carbon atoms of which 3–7 are ring carbon atoms in cycloalkyl and wherein m is an integer from zero to two, alkylcarbonato having 2–7 carbon atoms, carbamyloxy, or (mono- or di-alkyl)carbamyloxy having 2–9 carbon atoms;

$Y^2$ is hydrogen, alkyl having 1–6 carbon atoms, or $Ar^1$—$C_nH_{2n}$— wherein $n$ is an integer from zero to four and $Ar^1$ is phenyl or phenyl substituted by 1–3 members of the group consisting of alkyl having 1–4 carbon atoms, alkoxy having 1–4 carbon atoms, and dialkylamino having 2–8 carbon atoms; or $Y^1$ and $Y^2$ taken together represent oxo or ethylenedioxy;

$Q^2$ is alkyl having 1–7 carbon atoms, alkenyl having 2–5 carbon atoms, haloalkenyl having 2–5 carbon atoms and having 1–3 members of the group consisting of chlorine, fluorine, and bromine attached to ethylenic carbon, alkynyl having 2–5 carbon atoms, cycloalkyl—$C_qH_{2q}$— wherein $q$ is an integer from zero to three and wherein cycloalkyl has 3–7 ring carbon atoms and has a total of 3–10 carbon atoms, and $Ar^2$—$C_qH_{2q}$— wherein $q$ is an integer from zero to three and $Ar^2$ is phenyl or is phenyl substituted by amino, nitro, alkanoylamino having 1–6 carbon atoms, alkoxy having 1–4 carbon atoms, alkyl having 1–4 carbon atoms, halo, or trifluoromethyl;

$Z^2$ is hydrogen, hydroxy, one of the acyloxy groups defined by $Y^1$, alkoxy having 1–6 carbon atoms, difluoromethoxy, trifluoromethoxy, benzyloxy, or alkenyloxy having 3–6 carbon atoms; and $R^1$ and $R^2$ are members of the group consisting of hydrogen and alkyl having 1–4 carbon atoms.

2. A compound according to claim 1 wherein each of $R^1$ and $R^2$ is alkyl.

3. A compound according to claim 2 wherein $R^1$ and $R^2$ are each methyl.

4. A compound according to claim 1 wherein $R^1$ and $R^2$ are each hydrogen.

5. 1,2,3,4,5,6-Hexahydro-1-oxo-3-(Q²-CO-)-8-(Z²)-6-(R¹)-11-(R²)-2,6-methano-3-benzazocine having the formula

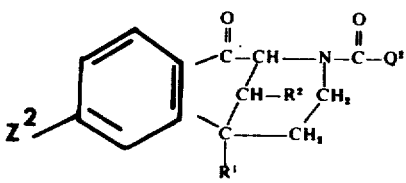

wherein:

Q² is alkyl having 1-7 carbon atoms, alkenyl having 2-5 carbon atoms, haloalkenyl having 2-5 carbon atoms and having 1-3 members of the group consisting of chlorine, fluorine, and bromine attached to ethylenic carbon, alkynyl having 2-5 carbon atoms, cycloalkyl—$C_qH_{2q}$— wherein $q$ is an integer from zero to three and wherein cycloalkyl has 3-7 ring carbon atoms and has a total of 3-10 carbon atoms, and Ar²—$C_qH_{2q}$— wherein $q$ is an integer from zero to three and Ar² is phenyl or is phenyl substituted by amino, nitro, alkanoylamino having 1-6 carbon atoms, alkoxy having 1-4 carbon atoms, alkyl having 1-4 carbon atoms, halo, or trifluoromethyl;

Z² is hydrogen; hydroxy; alkanoyloxy having 1-22 carbon atoms; alkenoyloxy having one or two double bonds and having 4-22 carbon atoms; Ar—$C_mH_{2m}$—CO—O— wherein $m$ is an integer from zero to two and Ar is phenyl or is phenyl substituted by 1-3 members of the group consisting of alkyl having 1-4 carbon atoms, alkoxy having 1-4 carbon atoms, halo, trifluoromethyl, dialkylamino having 2-8 carbon atoms, and alkanoylamino having 1-6 carbon atoms; phenoxyacetoxy; naphthalenecarbonyloxy; pyridinecarbonyloxy; (cycloalkyl or fluorocycloalkyl)—$C_mH_{2m}$—CO—O— having a total of 4-10 carbon atoms of which 3-7 are ring carbon atoms in cycloalkyl and wherein $m$ is an integer from zero to two, alkylcarbonato having 2-7 carbon atoms, carbamyloxy, or (mono- or di-alkyl)carbamyloxy having 2-9 carbon atoms; alkoxy having 1-6 carbon atoms; difluoromethoxy; trifluoromethoxy; benzyloxy; or alkenyloxy having 3-6 carbon atoms; and R¹ and R² are each alkyl having 1-4 carbon atoms.

6. 1,2,3,4,5,6-Hexahydro-1-oxo-3-(Q²-CO-)-8-(Z²)-6-(R¹)-11-(R²)-2,6-methano-3-benzazocine having the formula

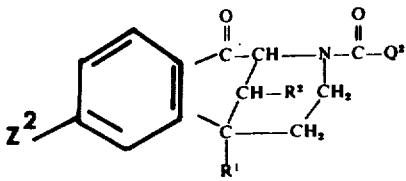

wherein:

Q² is cycloalkyl having 3-7 ring carbon atoms and a total of 3-10 carbon atoms;

Z² is hydrogen; hydroxy; alkanoyloxy having 1-22 carbon atoms; alkenoyloxy having one or two double bonds and having 4-22 carbon atoms; Ar—$C_mH_{2m}$—CO—O— wherein $m$ is an integer from zero to two and Ar is phenyl or is phenyl substituted by 1-3 members of the group consisting of alkyl having 1-4 carbon atoms, alkoxy having 1-4 carbon atoms, halo, trifluoromethyl, dialkylamino having 2-8 carbon atoms, and alkanoylamino having 1-6 carbon atoms; phenoxyacetoxy; naphthalenecarbonyloxy; pyridinecarbonyloxy; (cycloalkyl or fluorocycloalkyl)—$C_mH_{2m}$—CO—O— having a total of 4-10 carbon atoms of which 3-7 are ring carbon atoms in cycloalkyl and wherein $m$ is an integer from zero to two, alkylcarbonato having 2-7 carbon atoms, carbamyloxy, or (mono- or di-alkyl)carbamyloxy having 2-9 carbon atoms; alkoxy having 1-6 carbon atoms; difluoromethoxy; trifluoromethoxy; benzyloxy; or alkenyloxy having 3-6 carbon atoms; and R¹ and R² are each alkyl having 1-4 carbon atoms.

7. A compound according to claim 6 wherein Z² is hydrogen.

8. A compound according to claim 6 wherein Z² is hydroxy.

9. 1,2,3,4,5,6-Hexahydro-1-oxo-3-cyclopropanecarbonyl-8-(Z²)-6-(R¹)-11-(R²)-2,6-methano-3-benzazocine having the formula

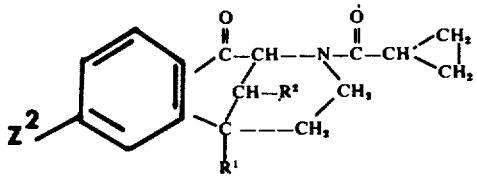

wherein:

Z² is hydrogen; hydroxy; alkanoyloxy having 1-22 carbon atoms; alkenoyloxy having one or two double bonds and having 4-22 carbon atoms; Ar—$C_mH_{2m}$—CO—O— wherein $m$ is an integer from zero to two and Ar is phenyl or is phenyl substituted by 1-3 members of the group consisting of alkyl having 1-4 carbon atoms, alkoxy having 1-4 carbon atoms, halo, trifluoromethyl, dialkylamino having 2-8 carbon atoms, and alkanoylamino having 1-6 carbon atoms; phenoxyacetoxy; naphthalenecarbonyloxy; pyridinecarbonyloxy; (cycloalkyl or fluorocycloalkyl)—$C_mH_{2m}$—CO—O— having a total of 4-10 carbon atoms of which 3-7 are ring carbon atoms in cycloalkyl and wherein $m$ is an integer from zero to two, alkylcarbonato having 2-7 carbon atoms, carbamyloxy, or (mono- or di-alkyl)carbamyloxy having 2-9 carbon atoms; alkoxy having 1-6 carbon atoms; difluoromethoxy; trifluoromethoxy; benzyloxy; or alkenyloxy having 3-6 carbon atoms; and R¹ and R² are each alkyl having 1-4 carbon atoms.

10. A compound according to claim 9 wherein R¹ and R² are each methyl.

11. 1,2,3,4,5,6-Hexahydro-1-oxo-3-cyclopropanecarbonyl-8-cyclopropanecarbonyloxy-6,11-dimethyl-2,6-methano-3-benzazocine.

* * * * *